(12) United States Patent
Düx et al.

(10) Patent No.: US 8,039,659 B2
(45) Date of Patent: Oct. 18, 2011

(54) PROCESSES FOR PREPARING DIARYL AND/OR ALKYLARYL CARBONATES FROM DIALKYL CARBONATES

(75) Inventors: Andre Düx, Brühl (DE); Pieter Ooms, Krefeld (DE); Johann Rechner, Kempen (DE); Matthias Böhm, Leverkusen (DE); Kaspar Hallenberger, Leverkusen (DE); Georg Ronge, Düsseldorf (DE); Johan Vanden Eynde, Zwijnaarde (BE)

(73) Assignee: Bayer MaterialScience AG, Leverkusen (DE)

( * ) Notice: Subject to any disclaimer, the term of this patent is extended or adjusted under 35 U.S.C. 154(b) by 322 days.

(21) Appl. No.: 12/210,279

(22) Filed: Sep. 15, 2008

(65) Prior Publication Data

US 2009/0076293 A1 Mar. 19, 2009

(30) Foreign Application Priority Data

Sep. 14, 2007 (DE) .................... 10 2007 044 033

(51) Int. Cl.
*C07C 69/96* (2006.01)
(52) U.S. Cl. ...................................... 558/274
(58) Field of Classification Search .................. 558/274
See application file for complete search history.

(56) References Cited

U.S. PATENT DOCUMENTS

| | | | |
|---|---|---|---|
| 5,334,742 A | | 8/1994 | Schon et al. |
| 5,344,954 A | * | 9/1994 | Schon et al. ............... 558/274 |
| 7,288,668 B2 | * | 10/2007 | Ryu et al. .................. 558/274 |
| 2008/0221348 A1 | | 9/2008 | Fukuoka et al. |

FOREIGN PATENT DOCUMENTS

| | | |
|---|---|---|
| DE | 4226755 A1 | 2/1994 |
| DE | 4226756 A1 | 2/1994 |
| EP | 0461274 A1 | 12/1991 |
| EP | 0781760 A1 | 7/1997 |
| EP | 1795522 A1 | 6/2007 |
| JP | 2020351 A | 1/1990 |
| WO | WO-2004016577 A1 | 2/2004 |
| WO | WO-2006/001256 A1 | 1/2006 |

OTHER PUBLICATIONS

Agrawal, R., et al., "On the Use of Intermediate Reboilers in the Rectifying Section and Condensers in the Stripping Section of a Distillation Column", Ind. Eng. Chem. Res., vol. 35, (1996), pp. 2801-2807.

* cited by examiner

*Primary Examiner* — Rei-tsang Shiao
(74) *Attorney, Agent, or Firm* — Connolly Bove Lodge & Hutz LLP

(57) ABSTRACT

Processes comprising: reacting a dialkyl carbonate and an aromatic hydroxy compound in the presence of a transesterification catalyst in a first reaction column, the first reaction column comprising a top section, a bottom section, a rectifying section in an upper portion of the column and a reaction zone below the rectifying section; feeding a bottom product from the first reaction column to a further reaction column; the bottom product comprising a diaryl carbonate, an alkylaryl carbonate, or both, and residual unreacted dialkyl carbonate and aromatic hydroxy compound; the further reaction column comprising a top section, a rectifying section in an upper portion of the column and a reaction zone below the rectifying section; and reacting the residual unreacted dialkyl carbonate and aromatic hydroxy compound in the further reaction column; feeding a process stream to a distillation column, the process stream comprising a mixture of unreacted dialkyl carbonate and one or more reaction-product alcohols drawn from the first reaction column, the further reaction column, or both, such that the unreacted dialkyl carbonate is separated from the one or more reaction-product alcohols; and recycling the separated, unreacted dialkyl carbonate to the first reaction column; wherein the further reaction column comprises one or more condensers, and heat of condensation from the one or more condensers is fed back into the process.

18 Claims, 4 Drawing Sheets

PROCESSES FOR PREPARING DIARYL AND/OR ALKYLARYL CARBONATES FROM DIALKYL CARBONATES

BACKGROUND OF THE INVENTION

The preparation of aromatic and aliphatic-aromatic carbonic acid esters (carbonates) by transesterification starting from aliphatic carbonic acid esters and aromatic hydroxy compounds has been described. Such preparative methods are equilibrium reactions in which the position of equilibrium is shifted almost completely towards the aliphatically substituted carbonates. It is therefore comparatively simple to prepare aliphatic carbonates from aromatic carbonates and alcohols. However, in order to carry out the reactions in the opposite direction, in the direction towards aromatic carbonates, it is necessary to shift the equilibrium, which is positioned very unfavorably, to the side of the aromatic carbonates, it being necessary to use not only very active catalysts but also suitable procedures.

Carrying out such equilibrium reactions in columns and thus advantageously shifting them towards the formation of the desired product has been described, for example, in: U. Block, Chem.-Ing. Techn. 49, 151 (1977); DE-OS 38 09 417; B. Sehleper, B. Gutsche, J. Wnuck and L. Jeromin, Chem.-Ing.-Techn. 62, 226 (1990); Ullmanns Encyclopädie der techn. Chemie, 4th Edition, Vol. 3; p. 375 ff. (1973).

In the described processes, the transesterification is therefore also preferably carried out continuously as a countercurrent transesterification in one or more reaction columns.

EP-A 0 461 274 describes a continuous transesterification process for the preparation of aromatic carbonates in one or in a plurality of multistage columns connected in series, wherein dialkyl carbonates or alkylaryl carbonates are reacted with phenols and the readily volatile products, namely the reaction alcohols and dialkyl carbonates, are removed at the head (top) of the columns and the high-boiling products, such as, for example, diaryl carbonates, are removed at the bottom of the columns. However, there is no direction as to the manner or extent to which heat produced in this process can be further used.

DE-A 42 26 756 describes a two-stage process for the preparation of diaryl carbonates by transesterification of a dialkyl carbonate with an aromatic hydroxy compound, in which the corresponding alkylaryl carbonate is first formed from the starting materials in a first stage and the diaryl carbonate is formed in a second stage. The information given in the process description is limited to the reaction conditions, the catalyst used and the construction of the reaction columns. No information is given, however, regarding the manner or extent to which heat produced in this process can be further used.

DE-A 42 26 755 describes a process for the preparation of diaryl carbonates in two reaction columns which are coupled with one another in terms of energy and materials, wherein an aromatic hydroxy compound and a dialkyl carbonate are reacted in the first stage, and the alkylaryl carbonate formed thereby is converted into the diaryl carbonate in the second stage either by transesterification with the aromatic hydroxy compound or by disproportionation. However, a problem with this process is that, owing to the integration of the process in terms of materials and energy, the reaction conditions for the formation of the alkylaryl or diaryl carbonate cannot be chosen optimally because they are determined by the almost identical pressure prevailing in the two steps.

EP-A 781 760 describes a continuous process for the preparation of aromatic carbonates by reacting a dialkyl carbonate with an aromatic hydroxy compound in the presence of a catalyst and continuously removing the aromatic carbonate formed in the reaction, the alcoholic secondary products, the dialkyl carbonate and the aromatic hydroxy compound, the dialkyl carbonate and the aromatic hydroxy compound being fed back into the reaction again. Although the described process steps are effective as regards the reaction procedure in terms of a high space-time yield and as regards working-up in terms of an efficient a separating sequence as possible, the process does not exhibit any possibilities for integration of the reaction and the working-up steps in terms of energy.

WO-A 2006/001256 describes a process in which an aromatic hydroxy compound is reacted with a dialkyl carbonate in the presence of a catalyst, as well as a technical device suitable therefor. Here too, no reference points are given for energy integration.

Without appropriately efficient energy integration, the energy consumption of the processes described hereinbefore is known to be high, which in turn raises questions about the advantageousness of the phosgene-free preparation of aryl carbonates from an ecological and economic point of view.

WO-A 2004/016577 describes a process for the preparation of aromatic carbonates from dialkyl carbonate and an aromatic hydroxy compound in the presence of a catalyst in a plurality of separate, series-connected reaction zones of a reactor arrangement, wherein the heat of condensation that is formed in the condensation of the vapor stream of the last reaction zone is used to heat the liquid stream introduced into the first reaction zone. However, this process has the disadvantage that the reactor arrangement is complex. In addition, the energy integration of this process is worthy of improvement.

JP-A 2002-020351 describes a discontinuous process for the preparation of diaryl carbonate, from which heat can be used for the production of steam. Disadvantages of this process are, however, that it is carried out discontinuously and the reactor arrangement used for the reaction with a distillation column mounted on top. However, a particular disadvantage of this process is that it is carried out discontinuously.

BRIEF SUMMARY OF THE INVENTION

The present invention relates to processes for the preparation of diaryl carbonates and/or alkylaryl carbonates from dialkyl carbonates and aromatic hydroxy compounds using at least two reaction columns, wherein the heat of condensation from condensers associated with one or more of these columns is fed back to and used in the process.

Accordingly, the various embodiments of the invention provide processes for the preparation of aromatic carbonates, i.e. diaryl and/or alkylaryl carbonates, especially diaryl carbonates, which do not exhibit the above-mentioned disadvantages and in which, as compared with the known processes mentioned hereinbefore, energy integration is possible in an efficient manner, or improved energy integration can be achieved.

The various embodiments of the invention provide processes for the preparation of aromatic carbonates, which by suitable heat integration, provide markedly reduced energy consumption in the preparation of aromatic carbonates from dialkyl carbonates and aromatic hydroxy compounds in at least two reaction columns.

The present invention relates, in particular, to processes for the preparation of at least one diaryl carbonate and/or alkylaryl carbonate from at least one dialkyl carbonate and at least one aromatic hydroxy compound, wherein (a) the dialkyl carbonate(s) is/are reacted in the presence of at least one transesterification catalyst with the aromatic hydroxy compound(s) in a first reaction column containing at least one rectifying section in the upper portion of the column and at least one reaction zone beneath the rectifying section, which has at least two sections, (b) the vapor removed at the top of the first reaction column is condensed wholly or partially in at least one condenser, (c) the bottom product of the first reaction column is fed to at least one further reaction column containing at least one rectifying section in the upper portion of the column and at least one reaction zone beneath the rectifying section and is reacted further therein, (d) the dialkyl carbonate that has not been reacted in the reaction columns or that has formed during the reaction is separated wholly or partially from the alkyl alcohol formed during the reaction in at least one further process step containing at least one distillation column, and (e) the dialkyl carbonate separated off under (d), optionally after further purification, is fed to the first reaction column again, characterized in that the further reaction column(s) is/are equipped with one or more condensers, and the heat of condensation obtained by condensation in these condensers is fed directly or indirectly back into the process again.

One embodiment of the present invention includes processes which comprise:

reacting a dialkyl carbonate and an aromatic hydroxy compound in the presence of a transesterification catalyst in a first reaction column, the first reaction column comprising a top section, a bottom section, a rectifying section in an upper portion of the column and a reaction zone below the rectifying section;

feeding a bottom product from the first reaction column to a further reaction column; the bottom product comprising a diaryl carbonate, an alkylaryl carbonate, or both, and residual unreacted dialkyl carbonate and aromatic hydroxy compound; the further reaction column comprising a top section, a rectifying section in an upper portion of the column and a reaction zone below the rectifying section; and reacting the residual unreacted dialkyl carbonate and aromatic hydroxy compound in the further reaction column;

feeding a process stream to a distillation column, the process stream comprising a mixture of unreacted dialkyl carbonate and one or more reaction-product alcohols drawn from the first reaction column, the further reaction column, or both, such that the unreacted dialkyl carbonate is separated from the one or more reaction-product alcohols; and recycling the separated, unreacted dialkyl carbonate to the first reaction column;

wherein the further reaction column comprises one or more condensers, and heat of condensation from the one or more condensers is fed back into the process.

BRIEF DESCRIPTION OF THE SEVERAL VIEWS OF THE DRAWING

The foregoing summary, as well as the following detailed description of the invention, may be better understood when read in conjunction with the appended drawings. For the purpose of assisting in the explanation of the invention, there are shown in the drawings representative embodiments which are considered illustrative. It should be understood, however, that the invention is not limited in any manner to the precise arrangements and instrumentalities shown.

In the drawings.

DETAILED DESCRIPTION OF THE INVENTION

Figure 1:
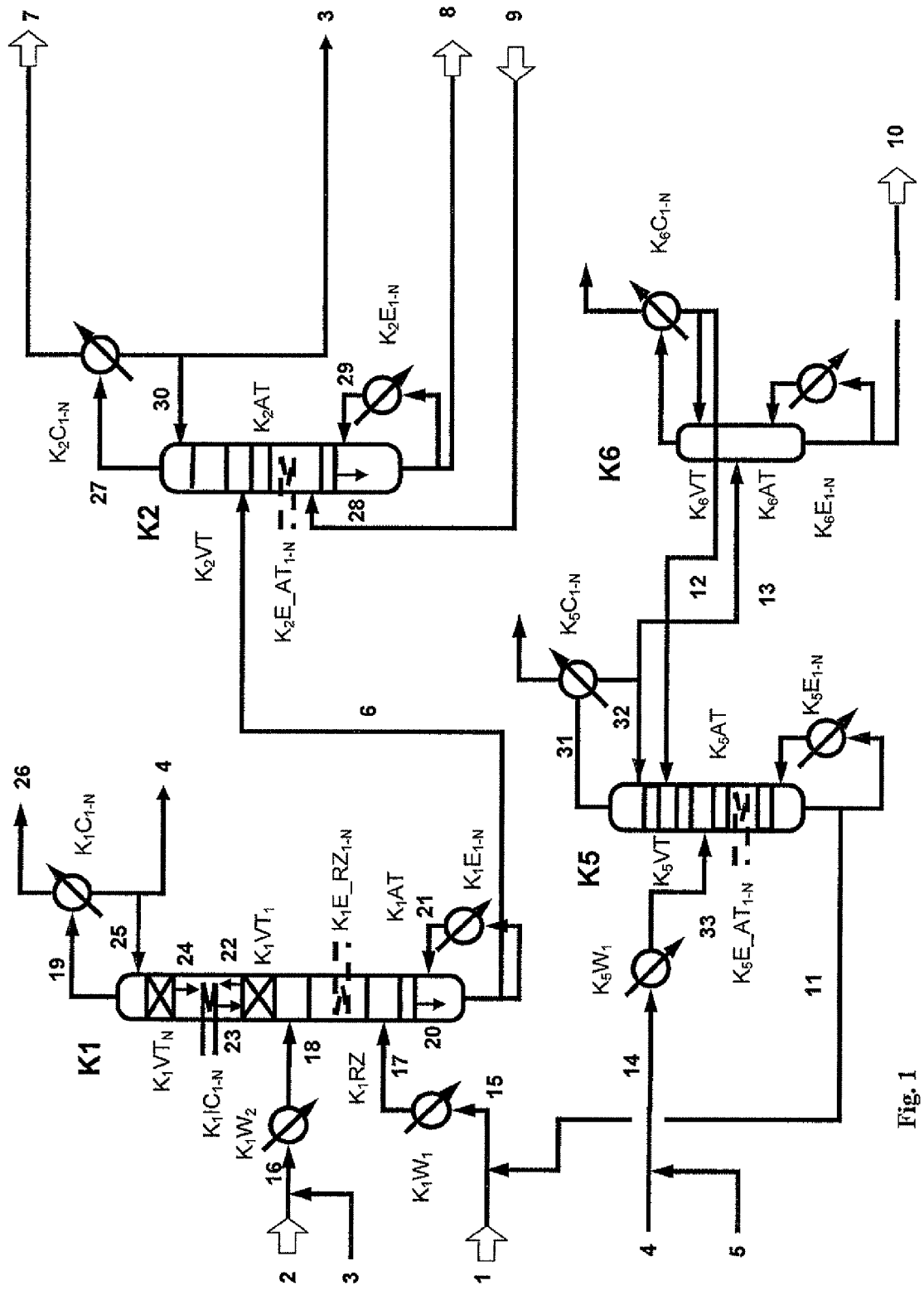
FIG. 1 is a schematic representation of one embodiment of a process according to the invention.

As used herein, the singular terms "a" and "the" are synonymous and used interchangeably with "one or more" and "at least one," unless the language and/or context clearly indicates otherwise. Accordingly, for example, reference to "a condenser" herein or in the appended claims can refer to a single condenser or more than one condenser. Similarly, for example, reference to "a dialkyl carbonate" herein or in the appended claims can refer to a single dialkyl carbonate or more than one dialkyl carbonate. As used herein, terms of positional disposition, such as, for example, "below," "above," and "between" do not require absolute vertical alignment or immediacy. Thus, for example, one zone disposed below another zone does not require that the two be vertically aligned or that they be directly adjacent, rather only that the one zone is lower than the other zone with respect to relative height. Similarly, an element which is "between" two other elements does not require that all three be consecutively adjacent or that the three elements be aligned. Additionally, all numerical values, unless otherwise specifically noted, are understood to be modified by the word "about."

Diaryl carbonates prepared within the scope of the invention include those of the general formula (I)

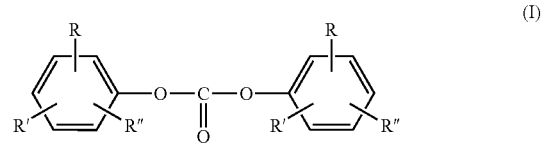

(I)

wherein R, R' and R" independently of one another represent H, linear or branched, optionally substituted $C_1$-$C_{34}$-alkyl, preferably $C_1$-$C_6$-alkyl, particularly preferably $C_1$-$C_4$-alkyl, $C_1$-$C_{34}$-alkoxy, preferably $C_1$-$C_6$-alkoxy, particularly preferably $C_1$-$C_4$-alkoxy, $C_5$-$C_{34}$-cycloalkyl, $C_7$-$C_{34}$-alkylaryl, $C_6$-$C_{34}$-aryl or a halogen radical, preferably a chlorine radical, and R, R' and R" on both sides of formula (I) can be the same or different. R can also represent —COO—R'", wherein R'" can be H, optionally branched $C_1$-$C_{34}$-alkyl, preferably $C_1$-$C_6$-alkyl, particularly preferably $C_1$-$C_4$-alkyl, $C_1$-$C_{34}$-alkoxy, preferably $C_1$-$C_6$-alkoxy, particularly preferably $C_1$-$C_4$-alkoxy, $C_5$-$C_{34}$-cycloalkyl, $C_7$-$C_{34}$-alkylaryl or $C_6$-$C_{34}$-aryl. Preferably, R, R' and R" on both sides of formula (I) are the same. Very particularly preferably, R, R' and R" represent H.

Diaryl carbonates of the general formula (I) include, for example: diphenyl carbonate, methylphenyl-phenyl carbonates and di-(methylphenyl)carbonates, also in the form of a mixture, wherein the methyl group can be in any desired position on the phenyl rings, as well as dimethylphenyl-phenyl carbonates and di-(dimethylphenyl) carbonates, also in the form of a mixture, wherein the methyl groups can be in any desired position on the phenyl rings, chlorophenyl-phenyl carbonates and di-(chlorophenyl)carbonates, wherein the methyl group can be in any desired position on the phenyl rings, 4-ethylphenyl-phenyl carbonate, di-(4-ethylphenyl) carbonate, 4-n-propylphenyl-phenyl carbonate, di-(4-n-propylphenyl)carbonate, 4-isopropylphenyl-phenyl carbonate, di-(4-isopropylphenyl)carbonate, 4-n-butylphenyl-phenyl carbonate, di-(4-n-butylphenyl)carbonate, 4-isobutylphenyl-phenyl carbonate, di-(4-isobutylphenyl)carbonate, 4-tert-butylphenyl-phenyl carbonate, di-(4-tert-butylphenyl)carbonate, 4-n-pentylphenyl-phenyl carbonate, di-(4-n-pentylphenyl)carbonate, 4-n-hexylphenyl-phenyl carbonate, di-(4-n-hexylphenyl)carbonate, 4-isooctylphenyl-phenyl carbonate, di-(4-isooctylphenyl)carbonate, 4-n-nonylphenyl-phenyl carbonate, di-(4-n-nonylphenyl)carbonate, 4-cyclohexylphenyl-phenyl carbonate, di-(4-cyclohexylphenyl) carbonate, 4-(1-methyl-1-phenylethyl)-phenyl-phenyl carbonate, di-[4-(1-methyl-1-phenylethyl)-phenyl]carbonate, biphenyl-4-yl-phenyl carbonate, di-(biphenyl-4-yl)carbonate, (1-naphthyl)-phenyl carbonate, (2-naphthyl)-phenyl carbonate, di-(1-naphthyl)carbonate, di-(2-naphthyl)carbonate, 4-(1-naphthyl)-phenyl-phenyl carbonate, 4-(2-naphthyl)-phenyl-phenyl carbonate, di-[4-(1-naphthyl)-phenyl] carbonate, di-[4-(2-naphthyl)phenyl]carbonate, 4-phenoxyphenyl-phenyl carbonate, di-(4-phenoxyphenyl) carbonate, 3-pentadecylphenyl-phenyl carbonate, di-(3-pentadecylphenyl)carbonate, 4-tritylphenyl-phenyl carbonate, di-(4-tritylphenyl)carbonate, methyl salicylate-phenyl carbonate, di-(methyl salicylate)carbonate, ethyl salicylate-phenyl carbonate, di-(ethyl salicylate)carbonate, n-propyl salicylate-phenyl carbonate, di-(n-propyl salicylate)carbonate, isopropyl salicylate-phenyl carbonate, di-(isopropyl salicylate)carbonate, n-butyl salicylate-phenyl carbonate, di-(n-butyl salicylate)carbonate, isobutyl salicylate-phenyl carbonate, di-(isobutyl salicylate)carbonate, tert-butyl salicylate-phenyl carbonate, di-(tert-butyl salicylate)carbonate, di-(phenyl salicylate)-carbonate and di-(benzyl salicylate) carbonate.

Preferred diaryl carbonates include: diphenyl carbonate, 4-tert-butylphenyl-phenyl carbonate, di-(4-tert-butylphenyl) carbonate, biphenyl-4-yl-phenyl carbonate, di-(biphenyl-4-yl)carbonate, 4-(1-methyl-1-phenylethyl)-phenyl-phenyl carbonate and di-[4-(1-methyl-1-phenylethyl)-phenyl]carbonate. Diphenyl carbonate is particularly preferred.

Dialkyl carbonates which can be used within the scope of the invention include those of formula (II)

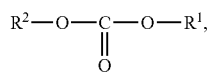
(II)

wherein $R^1$ and $R^2$ independently of one another represent linear or branched, optionally substituted $C_1$-$C_{34}$-alkyl, preferably $C_1$-$C_6$-alkyl, particularly preferably $C_1$-$C_4$-alkyl. $R^1$ and $R^2$ can be the same or different. $R^1$ and $R^2$ are preferably the same.

Preferred dialkyl carbonates include dimethyl carbonate, diethyl carbonate, di(n-propyl)carbonate, di(isopropyl)carbonate, di(n-butyl)carbonate, di(sec-butyl)carbonate, di(tert-butyl)carbonate or dihexyl carbonate. Dimethyl carbonate and diethyl carbonate are particularly preferred. Dimethyl carbonate is very particularly preferred.

Aromatic hydroxy compounds that are suitable within the scope of the invention include those of the general formula (III)

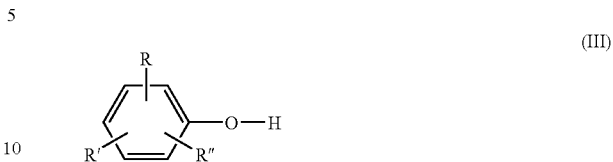
(III)

wherein R, R' and R" independently of one another can have the meaning given for the general formula (I).

Such aromatic hydroxy compounds are, for example: phenol, o-, m- or p-cresol, also in the form of a mixture of the cresols, dimethylphenol, also in the form of a mixture, wherein the methyl groups can be in any desired position on the phenol ring, e.g. 2,4-, 2,6- or 3,4-dimethylphenol, o-, m- or p-chlorophenol, o-, m- or p-ethylphenol, o-, m- or p-n-propylphenol, 4-isopropylphenol, 4-n-butylphenol, 4-isobutylphenol, 4-tert-butylphenol, 4-n-pentylphenol, 4-n-hexylphenol, 4-isooctylphenol, 4-n-nonylphenol, o-, m- or p-methoxyphenol, 4-cyclohexylphenol, 4-(1-methyl-1-phenylethyl)-phenol, biphenyl-4-ol, 1-naphthol, 2-1-naphthol, 4-(1-naphthyl)phenol, 4-(2-naphthyl)phenol, 4-phenoxyphenol, 3-pentadecylphenol, 4-tritylphenol, methylsalicylic acid, ethylsalicylic acid, n-propylsalicyclic acid, isopropylsalicylic acid, n-butylsalicylic acid, isobutylsalicylic acid, tert-butylsalicylic acid, phenylsalicylic acid and benzylsalicylic acid.

Preferred aromatic hydroxy compounds include phenol, 4-tert-butylphenol, biphenyl-4-ol and 4-(1-methyl-1-phenylethyl)-phenol. Phenol is particularly preferred.

Alkylaryl carbonates prepared within the scope of the invention include those of the general formula (IV)

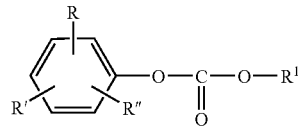

wherein R, R' and R" can have the meaning given for the general formula (I) and $R^1$ can have the meaning given for the general formula (II).

Preferred alkylaryl carbonates include methyl-phenyl carbonate, ethyl-phenyl carbonate, propyl-phenyl carbonate, butylphenyl carbonate and hexyl-phenyl carbonate, methyl-(o-cresyl)carbonate, methyl-(p-cresyl)carbonate, ethyl-(o-cresyl)carbonate, ethyl-β-cresyl)carbonate, methyl- or ethyl-(p-chlorophenyl)carbonate. Particularly preferred alkylaryl carbonates are methyl-phenyl carbonate and ethyl-phenyl carbonate. Methyl-phenyl carbonate is very particularly preferred.

Both the dialkyl carbonates suitable for the process according to the invention and the aromatic hydroxy compounds are known to the person skilled in the art and are commercially available, or can be prepared by processes which are likewise known to the person skilled in the art.

$C_1$-$C_4$-alkyl within the scope of the invention represents, for example, methyl, ethyl, n-propyl, isopropyl, n-butyl, sec-butyl, tert-butyl, $C_1$-$C_6$-alkyl additionally represents, for example, n-pentyl, 1-methylbutyl, 2-methylbutyl, 3-methylbutyl, neopentyl, 1-ethylpropyl, cyclohexyl, cyclopentyl, n-hexyl, 1,1-dimethylpropyl, 1,2-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl or 1-ethyl-2-methylpropyl, $C_1$-$C_{34}$-alkyl additionally represents, for example, n-heptyl and n-octyl, pinacyl, adamantyl, the isomeric menthyls, n-nonyl, n-decyl, n-dodecyl, n-tridecyl, n-tetradecyl, n-hexadecyl or n-octadecyl. The same applies for the corresponding alkyl radical in, for example, aralkyl or alkylaryl radicals. Alkylene radicals in the corresponding hydroxyalkyl or aralkyl or alkylaryl radicals represent, for example, the alkylene radicals corresponding to the above alkyl radicals.

Aryl represents a carbocyclic aromatic radical having from 6 to 34 skeletal carbon atoms. The same applies for the aromatic part of an arylalkyl radical, also referred to as an aralkyl radical, as well as for aryl constituents of more complex groups, such as, for example, arylcarbonyl radicals.

Arylalkyl and aralkyl, each independently of the other, denote a straight-chained, cyclic, branched or unbranched alkyl radical according to the above definition which can be monosubstituted, polysubstituted or completely substituted by aryl radicals according to the above definition.

The above lists are given by way of example, without implying any limitation.

In the processes according to the invention, the aromatic hydroxy compound(s) and the dialkyl carbonate(s) can be reacted in the first reaction column in a molar ratio of preferably from 1:0.1 to 1:10, particularly preferably from 1:0.2 to 1:5, very particularly preferably from 1:0.5 to 1:3. The indicated molar ratio does not take into account the feeding of aromatic hydroxy compound or dialkyl carbonate back into the reaction column via one or more top condenser(s) (see under (b)) or one or more bottom evaporator(s) which may be present.

The various embodiments of processes according to the invention are carried out in at least two reaction columns.

Columns known to the person skilled in the art are suitable as the first and second column or as optional third or further column(s). These are, for example, distillation or rectification columns, preferably reactive distillation or reactive rectification columns.

The first reaction column contains at least one rectifying section in the upper portion of the column and at least one reaction zone below the rectifying section, which preferably has at least two sections. Each of the two sections, independently of the other, has preferably from 0 to 20, more preferably from 0.1 to 20, theoretical stages. In preferred embodiments, at least one rectifying section of the first reaction column is equipped with at least one intermediate condenser. The intermediate condenser is preferably arranged between the two sections of the rectifying section. In that case, the rectifying section is divided into an upper and a lower rectifying section.

The first reaction column is preferably operated countercurrrently, the aromatic hydroxy compound preferably being guided in liquid form in at least one reaction zone of the column from the top to the bottom and the dialkyl carbonate in gaseous form being guided countercurrently to the liquid stream. The first reaction column is preferably operated in such a manner that there are fed into at least one reaction zone, preferably into the top third of the reaction zone, preferably at the temperature prevailing at that point of the column, one or more streams containing the aromatic hydroxy compound and optionally dissolved transesterification catalyst, in liquid form or with only a low gas content, the gas content preferably being less than 20 wt. %. In addition, one or more streams containing the dialkyl carbonate are fed to the reaction zone, preferably in the bottom third of the reaction zone, and preferably in gaseous or superheated form. In preferred embodiments, superheating of the vapor stream can be from 0 to 50° C. Furthermore, the temperature of dewpoint is preferably governed by the pressure prevailing in the reaction zone at the point of addition of the particular stream containing dialkyl carbonate.

After passing through the reaction zone(s), the alkyl alcohol formed during the reaction, after passing through the rectifying section or sections, is removed at the top of the first reaction column. Within the scope of the invention, the alkyl alcohol formed during the reaction, also known as the reaction alcohol, is the alcohol formed in the transesterification, preferably $R^1$—OH or $R^2$—OH, where $R^1$ and $R^2$ have the meaning given for the general formula (II). In addition to the alkyl alcohol formed during the reaction, the stream removed at the top of the first reaction column generally also contains excess or unreacted dialkyl carbonate and low-boiling secondary compounds, such as, for example, carbon dioxide or dialkyl ethers. Owing to the rectifying section(s) present, this stream contains only small amounts of higher-boiling components, such as, for example, the aromatic hydroxy compound. The rectifying section serves to separate the higher-boiling components which are also evaporated in the reaction zone, such as, for example, the aromatic hydroxy compound or alkylaryl carbonate, from the low-boiling reaction alcohols or dialkyl carbonates. This has the advantage that the separation of the alkyl alcohols formed during the reaction from the dialkyl carbonates can be carried out at a low temperature level.

In preferred embodiments, the first reaction column is operated under reflux conditions. Reflux conditions are to be understood as meaning a procedure in which the vapor stream is condensed partially or completely at the top end of the rectifying section (see under b)) and some or all of the condensate formed thereby is fed back at the top end of the rectifying section again as reflux. The reflux ratio is preferably from 0.1 to 20, particularly preferably from 0.1 to 10 and very particularly preferably from 0.1 to 3, the reflux ratio within the scope of the invention corresponding to the weight ratio of condensate fed back into the column to vapor removed at the top of the column without returned condensate.

In preferred embodiments, the first reaction column has at least one stripping part beneath a reaction zone.

The first reaction column can preferably further be equipped with one or more bottom evaporator(s). When the transesterification column is constructed with a stripping section, a bottom evaporator is preferably also used, the bottom evaporator wholly or partially evaporating the liquid flowing from the stripping section. All or part of this wholly or partially evaporated liquid stream is fed back into the first reaction column again. In the case of an embodiment without a stripping section, the liquid flowing from the reaction zone is evaporated wholly or partially in a bottom evaporator which is optionally used, and all or part thereof is fed back into the first reaction column again.

In preferred embodiments, in which at least one rectifying section of the first reaction column is equipped with at least one intermediate condenser, the rectifying section is divided into a lower and an upper rectifying section (two sections), of which the lower rectifying section is located beneath the intermediate condenser and the upper rectifying section is located above the intermediate condenser.

In preferred embodiments, the rectifying section(s) having at least one intermediate condenser can be accommodated in the reaction column together with the reaction part(s) and optionally at least one stripping section. The vaporous mixture leaving the reaction zone(s) is thereby guided from below into a lower section of the rectifying section, or optionally the lower rectifying section, wherein separation of the aromatic hydroxy compound takes place. The vaporous mixture leaving this lower section, or optionally the lower rectifying section, is guided into an intermediate condenser, where it partially condenses, and the resulting condensate is supplied at the top end of the lower section of the rectifying section, or optionally the lower rectifying section.

In a further preferred embodiment of the process according to the invention, the intermediate condenser is not integrated into the first reaction column but is in the form of a separate intermediate condenser outside the first reaction column.

In a further preferred embodiment of the process according to the invention, the intermediate condenser and the upper section of the rectifying section are not integrated into the reaction column but are accommodated separately outside the first reaction column.

Beneath the reaction zone and a stripping part that is optionally present, a mixture containing alkylaryl carbonate, excess or unreacted phenol diaryl carbonate, transesterification catalysts, dialkyl carbonate, reaction alcohol, and high-boiling compounds formed in the reaction or already present in the starting materials is obtained. When a stripping section is used, the content of low-boiling compounds, such as, for example, dialkyl carbonate and reaction alcohol, is reduced, further alkylaryl carbonate and/or diaryl carbonate being formed under some circumstances in the presence of the transesterification catalyst. The energy required therefor is preferably supplied by one or more evaporators.

In all sections of the first reaction column, that is to say in the rectifying section and optionally the stripping section as well as in the reaction zone, it is possible to use random or structured packing. The random or structured packing to be used are those which are conventional for distillations, as are described, for example, in Ullmann's Encyclopädie der Technischen Chemie, 4th Edition, Vol. 2, p. 528 ff. Examples of random packing which may be mentioned include Raschig or Pall and Novalox rings, Berl, Intalex or torus saddles, Inter-pack bodies, and examples of structured packing which may be mentioned include sheet metal and wire gauze packing (such as e.g. BX packing, Montz Pak, Mellapak, Melladur, Kerapak and CY packing) of various materials, such as glass, stoneware, porcelain, stainless steel, plastics material. Preference is given to random and structured packings which have a large surface area and exhibit good wetting as well as an adequate residence time of the liquid phase. These are, for example, Pall and Novalox rings, Berl saddles, BX packing, Montz Pak, Mellapak, Melladur, Kerapak and CY packing.

Alternatively, distillation trays, such as, for example, perforated plates (sieve trays), bubble-cap trays, valve trays and tunnel-type trays, are also suitable. In the reaction zone(s) of the reaction column, distillation trays having high residence times with good material exchange, for example bubble-cap trays, valve trays or tunnel-type trays having high overflow defences, are particularly preferred. The theoretical plate number of the reaction zone is preferably from 3 to 50, particularly preferably from 10 to 50 and very particularly preferably from 10 to 40. The liquid hold-up is preferably from 1 to 80%, particularly preferably from 5 to 70% and very particularly preferably from 7 to 60% of the inside volume of the column of the reaction zone. The more precise design of the reaction zone(s), of the stripping part that is optionally to be used and of the rectifying section(s) can be carried out by the person skilled in the art.

The temperature of the reaction zone(s) is preferably in the range from 100 to 300° C., particularly preferably from 120 to 250° C., very particularly preferably from 150 to 240° C. In preferred embodiments, an optimal reaction temperature is established in the reaction zone on the one hand by the choice of operating conditions and on the other hand by the additional supply of heat in the region of one or more reactive trays. The supply of heat at the reactive trays can take place either by means of heat exchangers or via reactive trays with the possibility of heat introduction. It is advantageous to carry out the transesterification according to the invention not only at normal pressure but also at elevated or reduced pressure. The pressure of the reaction zone is therefore preferably in the range from 0.5 to 20 bar (absolute), particularly preferably from 0.8 to 15 bar (absolute), very particularly preferably from 0.9 to 10 bar (absolute).

Transesterification catalysts known from the literature can be used for the reaction steps occurring in the first reaction column. These are transesterification catalysts known from the literature for dialkyl carbonate-phenol transesterification, such as, for example, hydrides, oxides, hydroxides, alcoholates, amides and other salts of alkali and alkaline earth metals, such as of lithium, sodium, potassium, rubidium, caesium, magnesium and calcium, preferably lithium, sodium, potassium, magnesium and calcium, and particularly preferably lithium, sodium and potassium (see e.g. U.S. Pat. No. 3,642,858, U.S. Pat. No. 3,803,201 or EP-A 1082). Salts of the alkali and alkaline earth metals can also be salts of organic or inorganic acids, such as of acetic acid, propionic acid, butyric acid, benzoic acid, stearic acid, carbonic acid (carbonates or hydrogen carbonates), phosphoric acid, hydrocyanic acid, thiocyanic acid, boric acid, cinnamic acid, $C_{14}$-stannonic acids or antimonic acid. Suitable compounds of the alkali and alkaline earth metals are preferably the oxides, hydroxides, alcoholates, acetates, propionates, benzoates, carbonates and hydrogen carbonates, with particular preference being given to the use of hydroxides, alcoholates, acetates, benzoates or carbonates. The mentioned alkali or alkaline earth metal compounds are preferably used in amounts of from 0.001 to 2 wt. %, more preferably from 0.005 to 0.9 wt. % and particularly preferably from 0.01 to 0.5 wt. %, based on the weight of the reaction mixture to be reacted.

Further catalysts which can be used according to the invention are metal compounds such as $AlX_3$, $TiX_3$, $UX_4$, $TiX_4$, $VOX_3$, $VX_5$, $ZnX_2$, $FeX_3$, $PbX_2$ and $SnX_4$, wherein X represents halogen, acetoxy, alkoxy or aryloxy radicals (DE-OS 2 58 412). Particularly preferred catalysts which can be used according to the invention are metal compounds such as $AlX_3$, $TiX_4$, $PbX_2$ and $SnX_4$, such as, for example, titanium tetrachloride, titanium tetramethoxide, titanium tetraphenoxide, titanium tetraethoxide, titanium tetraisopropylate, titanium tetradodecylate, tin tetraisooctylate and aluminum triisopropylate. Metal compounds $TiX_4$ are very particularly preferred. The mentioned metal compounds are preferably used in amounts of from 0.001 to 5 wt. %, more preferably from 0.005 to 5 wt. % and particularly preferably from 0.01 to 5 wt. %, based on the weight of the reaction mixture to be reacted.

Within the scope of the invention, halogen denotes fluorine, chlorine or bromine, preferably fluorine or chlorine, particularly preferably chlorine.

Further catalysts which can be used according to the invention are organotin compounds of the general formula $(R^{11})_{4-x}Sn(Y)$ in which Y represents a radical $OCOR^{12}$, OH or OR, wherein $R^{12}$ represents $C_1$-$C_{12}$-alkyl, $C_6$-$C_{12}$-aryl or $C_7$-$C_{13}$-alkylaryl, $R^{11}$ independently of $R^{12}$ has the meaning of $R^{12}$ and x represents an integer from 1 to 3, dialkyltin compounds having from 1 to 12 carbon atoms in the alkyl radical, or bis-(trialkyltin) compounds, for example trimethyltin acetate, triethyltin benzoate, tributyltin acetate, triphenyltin acetate, dibutyltin diacetate, dibutyltin dilaurate, dioctyltin dilaurate, dibutyltin adipinate, dibutyldimethoxytin, dimethyltin glycolate, dibutyldiethoxytin, triethyltin hydroxide, hexaethylstannoxane, hexabutylstannoxane, dibutyltin oxide, dioctyltin oxide, butyltin triisooctylate, octyltin triisooctylate, butylstannonic acid and octylstannonic acid in amounts of from 0.001 to 20 wt. % (see EP 879, EP 880, EP 39 452, DE-OS 34 45 555, JP 79/63023), polymeric tin compounds of the formula —[—RR$^{11}$Sn—O—]—, in which R and R$^{11}$ independently of one another have the meaning given above for $R^{12}$, for example poly[oxy(dibutylstannylene)], poly[oxy(dioctylstannylene)], poly[oxy(butylphenylstannylene)] and poly[oxy(diphenylstannylene)] (DE-OS 34 45 552), polymeric hydroxystannoxanes of the formula —[—RSn(OH)—O—]—, for example poly(ethylhydroxystannoxane), poly(butylhydroxystannoxane), poly(octylhydroxystannoxane), poly(undecylhydroxystannoxane) and poly(dodecylhydroxystannoxanes) in amounts of from 0.001 to 20 wt. %, preferably from 0.005 to 5 wt. %, based on dialkyl carbonate (DE-OS 40 06 520). Further tin compounds which can be used according to the invention are Sn(II) oxides of the general formula

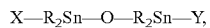

wherein X and Y independently of one another represent OH, SCN, OR$^{13}$, OCOR$^{13}$ or halogen and R represents alkyl, aryl, wherein R$^{13}$ has the meaning given above for $R^{12}$ (EP 0 338 760).

Further catalysts which can be used according to the invention are lead compounds, optionally together with triorganophosphanes, a chelate compound or an alkali metal halide, for example Pb(OH)$_2$-2PbCO$_3$, Pb(OCO—CH$_3$)$_2$, Pb(OCO—CH$_3$)$_2$.2LiCl, Pb(OCO—CH$_3$)$_3$.2PPh$_3$ in amounts of from 0.001 to 1, preferably from 0.005 to 0.25 mol per mol of dialkyl carbonate (JP 57/176932, JP 01/093580), as well as other lead (II) and lead (IV) compounds, such as PbO, PbO$_2$, red lead, plumbites and plumbates (JP 01/093560), iron (III) acetate (JP 61/1 72 852), also copper salts and/or metal complexes, for example of alkali, zinc, titanium and iron (JP 89/005588).

It is further possible to use heterogeneous catalyst systems in the process according to the invention. Such systems are, for example, mixed oxides of silicon and titanium which are obtainable by common hydrolysis of silicon and titanium halides (JP 54/125617) or titanium dioxides having a high BET surface area>20 m$^2$/g (DE-OS 40 36 594).

Preferred catalysts for the process according to the invention are the above-mentioned metal compounds AlX$_3$, TiX$_3$, UX$_4$, TiX$_4$, VOX$_3$, VX$_5$, ZnX$_2$, FeX$_3$, PbX$_2$ and SnX$_4$. Particular preference is given to AlX$_3$, TiX$_4$, PbX$_2$ and SnX$_4$, of which titanium tetrachloride, titanium tetramethoxide, titanium tetraphenoxide, titanium tetraethoxide, titanium tetraisopropylate, titanium tetradodecylate, tin tetraisooctylate and aluminium triisopropylate may be mentioned by way of example. Metal compounds TiX$_4$ are very particularly preferred. Particular preference is given to titanium tetramethoxide, titanium tetraphenoxide and titanium tetraethoxide.

The catalyst is preferably introduced into the first reaction column in dissolved or suspended form together with the stream containing the aromatic hydroxy compound(s). Alternatively, the catalyst can also be metered in separately, for example in an alcohol corresponding to the reaction alcohol or in a suitable inert solvent. When heterogeneous catalysts are used, these can be used in admixture with the mentioned filling materials, in a suitable form instead of random packing or as a bulk filling on any column plates fitted.

The energy required for the reaction in the first reaction column can on the one hand be produced via internal or external devices, such as, for example, heat exchangers, evaporators and/or heatable column plates, and/or on the other hand can be introduced either with the liquid stream containing the aromatic hydroxy compound(s) or with the dialkyl-carbonate-containing stream which is fed in gaseous form. A supply of heat can take place in this manner in particular in the region of the reaction zone(s). This heat in the region of the reaction zone(s) is preferably supplied wholly or partially by means of evaporators or heatable distillation trays. It is particularly advantageous to introduce the energy required for the reaction in the first reaction column into the first reaction column at least partially both with the liquid stream containing the aromatic hydroxy compound(s) and with the dialkyl-carbonate-containing stream fed in gaseous form and additionally by means of internal and/or external heat exchangers.

In the various embodiments of the process according to the invention, the bottom product of the first reaction column is fed to a second reaction column.

The second reaction column contains at least one rectifying section in the upper portion of the column and at least one reaction zone beneath the rectifying section. The rectifying section has preferably from 1 to 50, particularly preferably from 1 to 25, theoretical stages.

In the second reaction column, the bottom product of the first reaction column, which already contains alkylaryl carbonate and diaryl carbonate that have formed, is fed in liquid form or in the form of a vapor/liquid mixture preferably to the reaction zone, particularly preferably to the top part of the reaction zone, very particularly preferably into the top third of the reaction zone. The second reaction column is preferably operated in such a manner that the alkylaryl carbonate is reacted partially or completely, for example by further transesterification or disproportionation, preferably by disproportionation, to the diaryl carbonate. In addition to the bottom product of the first reaction column, one or more alkylaryl-carbonate-containing streams can be fed in in liquid form or in the form of a vapor/liquid mixture in the region of the reaction zone. Such additional alkylaryl-carbonate-containing streams can originate, for example, from the further refinery steps and can thus be fed back into the process.

Unreacted aromatic hydroxy compound, dialkyl carbonate, reaction alcohol, middle-boiling by-products—such as, for example, alkyl aryl ethers—and, to a small extent, low-boiling secondary compounds are separated off at the top of the second reaction column. Within the scope of the invention, middle-boiling by-products are to be understood as being those having a boiling point below that of the aromatic hydroxy compound and above that of the dialkyl carbonate. Such middle-boiling by-products are, for example, alkyl aryl ethers, such as, for example, anisole or phenetol. The middle-boiling by-products separated off in the second reaction column can be formed in the first and/or second reaction column in the reaction or can have already been introduced into the process by the starting materials.

The rectifying section of the second reaction column serves to separate off the higher-boiling components such as, for example, alkylaryl carbonate, which have also been evaporated in the reaction zone.

In preferred embodiments, the second reaction column is operated under reflux conditions. Reflux conditions are to be understood as meaning a procedure in which the vapor stream is condensed partially or completely at the top end of the rectifying section and some or all of the condensate formed thereby is fed back at the top end of the rectifying section again as reflux. The reflux ratio is preferably from 0.1 to 20, particularly preferably from 0.1 to 10 and very particularly preferably from 0.1 to 3, the reflux ratio within the scope of the invention corresponding to the weight ratio of condensate fed back into the column to vapor removed at the top of the column without returned condensate.

The second reaction column can comprise at least one stripping section beneath a reaction zone. In preferred embodiments, however, the reaction zone of the second reaction column can at the same time serve as the stripping section. The dialkyl carbonate freed in the disproportionation, reaction alcohol freed by transesterification and unreacted aromatic hydroxy compound are thereby separated off and, at the same time, diaryl carbonate and the alkylaryl carbonate reacting substantially to completion by disproportionation are concentrated.

The second reaction column can preferably further be equipped with one or more bottom evaporator(s).

In principle, the rectifying section of the second reaction column can likewise be equipped with one or more intermediate condensers. The rectifying section is thereby divided into a lower and an upper rectifying section (two sections), of which the lower rectifying section is located beneath the intermediate condenser and the upper rectifying section is located above the intermediate condenser. In a preferred embodiment, the second reaction column does not have an intermediate condenser.

The second reaction column is equipped with one or more condensers. These are preferably one or more condensers at the top of the second reaction column (top condenser(s)). A cascade of top condensers is preferably used.

During the condensation in the condenser(s) at the top of the second reaction column, the vapors become depleted of higher-boiling components, such as, for example, aromatic hydroxy compound. In order to be able to use the resulting heat of condensation particularly efficiently within the scope of a heat integration, the condensation is therefore preferably carried out in a plurality of stages, particularly preferably in at least two stages, in preferred embodiments in two or three stages.

In the particularly preferred embodiment of two- or three-stage condensation, the heat of condensation of the first or of the first and second condensation stage(s) is used directly or indirectly for heating a material stream or a column within the process, while the heat of condensation obtained in the second or third condensation stage is dissipated by cooling water or air cooling.

In further preferred embodiments, the condensation at the top of the second reaction column can additionally be carried out in such a manner that a portion of the vapors removed at the top of the second reaction column is not condensed, in order to permit the selective discharge of middle-boiling by-products.

Beneath the reaction zone and a stripping section that may optionally be present, a mixture containing alkylaryl carbonate, excess or unreacted aromatic hydroxy compound, diaryl carbonate, transesterification catalyst(s), dialkyl carbonate, reaction alcohol, and middle- or high-boiling by-products formed in the reaction or already present in the starting materials is obtained. Within the scope of the invention, high-boiling by-products are to be understood as being those having a boiling point above that of the aromatic hydroxy compound.

In all sections of the second reaction column, that is to say in the rectifying section and optionally the stripping part as well as in the reaction zone, it is possible to use random or structured packing. The random or structured packing to be used are those which are conventional for distillations, as are described, for example, in Ullmann's Encyclopädie der Technischen Chemie, 4th Edition, Vol. 2, p. 528 ff. Examples of random packing which may be mentioned include Raschig or Pall and Novalox rings, Berl, Intalex or torus saddles, Interpack bodies, and examples of regular packing which may be mentioned include sheet metal and woven packing (such as e.g. BX packing, Montz Pak, Mellapak, Melladur, Kerapak and CY packing) of various materials, such as glass, stoneware, porcelain, stainless steel, plastics material. Preference is given to random and structured packings which have a large surface area and exhibit good wetting as well as an adequate residence time of the liquid phase. These are, for example, Pall and Novolax rings, Berl saddles, EX packing, Montz Pak, Mellapak, Melladur, Kerapak and CY packing.

Alternatively, distillation trays, such as, for example, perforated plates (sieve trays), bubble-cap trays, valve trays and tunnel-type trays, are also suitable. In the reaction zone(s) of the second reaction column, bulk filling materials or structured packing are particularly preferred. The theoretical plate number of the reaction zone is preferably from 3 to 50, particularly preferably from 10 to 50 and very particularly preferably from 10 to 40.

The more precise design of the reaction zone(s), of the stripping section that is optionally to be used and of the rectifying section(s) can be carried out by the person skilled in the art.

The temperature of the reaction zone(s) is preferably in the range from 100 to 300° C., particularly preferably from 120 to 250° C., most particularly preferably from 180 to 250° C.

In particular embodiments, an optimal reaction temperature is established in the reaction zone on the one hand by the choice of operating conditions and on the other hand by the additional supply of heat in the region of one or more reactive trays. The supply of heat at the reactive trays can take place either by means of heat exchangers or via reactive trays with the possibility of heat introduction. It is advantageous to carry out the transesterification according to the invention not only at normal pressure but also at elevated or reduced pressure, preferably at reduced pressure. The pressure of the second reaction column is therefore preferably in the range from 0.05 to 20 bar (absolute), particularly preferably from 0.1 to 10 bar (absolute), very particularly preferably from 0.1 to 2 bar (absolute).

The transesterification catalysts already mentioned hereinbefore for the transesterification in the first reaction column can be used for the reaction steps carried out in the second reaction column. In a preferred embodiment, identical catalysts are used in the first and second reaction columns.

The catalyst is preferably introduced into the second reaction column in dissolved or suspended form together with the bottom product of the first reaction column. Alternatively, the catalyst can also be fed separately, for example in an alcohol corresponding to the reaction alcohol or in a suitable inert solvent. When heterogeneous catalysts are used, these can be used in admixture with the mentioned random and/or structured packing, in a suitable form instead of random and/or structured packing or as a bulk filling on any distillation trays fitted.

The energy required for the reaction in the second reaction column can on the one hand be produced via internal or external devices, such as, for example, heat exchangers, evaporators and/or heatable column plates, and/or on the other hand can be introduced with the liquid stream containing the aromatic hydroxy compound(s). This heat in the region of the reaction zone(s) is preferably supplied wholly or partially by means of evaporators.

The second reaction column can be followed by one or more further reaction columns. The conditions and parameter ranges mentioned hereinbefore for the second reaction column apply to such further reaction columns. However, the conditions and parameters for further reaction columns do not have to be identical with those in the second reaction column but preferably differ from those in the second reaction column within the scope of the conditions and parameter ranges mentioned hereinbefore. For example, an additional reaction column to the second reaction column is preferably operated at a lower pressure than the second reaction column; the reflux ratio and bottom temperature can also be changed compared with those in the second reaction column. In a preferred embodiment, the first reaction column in the process according to the invention is followed by only one further reaction column, that is to say the second reaction column mentioned hereinbefore. However, the reaction columns can be followed by further columns for purification and separation of the components of the streams that have been removed. Within the scope of the invention, such columns for purification and separation of the components are not understood as being reaction columns within the scope of the invention.

According to the invention, all or part of the heat of condensation obtained by condensation in the condenser(s), preferably top condenser(s), of the second or further reaction column(s), preferably of the second reaction column, is fed directly or indirectly back into the process again. Within the scope of the invention, the direct feeding of the heat of condensation back into the process is to be understood as meaning that the heat of condensation is fed back into the process without an intermediate heating medium, for example for heating either one or more streams or for heating one or more column sections within the process. This can take place, for example, in a heat exchanger. Preferably, such a heat exchanger is combined with the condenser(s). Within the scope of the invention, the indirect feeding of the heat of condensation back into the process is to be understood as meaning that a heating medium is first produced with the resulting heat of condensation, which heating medium is used to feed the heat of condensation back into the process. With this heating medium it is possible, for example, to heat one or more streams or one or more column sections within the process. Suitable heating media are gases, vapors or liquids, preferably vaporous or liquid technical heat carrier media such as, for example, water, heat carriers based on mineral oil, or synthetic heat carriers (e.g. Diphyl™, Marlotherm®). Particularly preferred heating media are water or water vapor.

According to the invention, in the case where the first reaction column is equipped with one or more intermediate condensers, all or part of the heat of condensation obtained by condensation in the intermediate condenser(s) is likewise fed directly or indirectly back into the process again. Within the scope of the invention, the direct feeding of the heat of condensation back into the process is to be understood as meaning that the heat of condensation is fed back into the process without an intermediate heating medium, for example for heating either one or more streams or for heating one or more column sections within the process. This can take place, for example, in a heat exchanger. Preferably, such a heat exchanger is combined with the intermediate condenser. Within the scope of the invention, the indirect feeding of the heat of condensation back into the process is to be understood as meaning that a heating medium is first produced with the resulting heat of condensation, which heating medium is used to feed the heat of condensation back into the process. With this heating medium it is possible, for example, to heat one or more streams or one or more column sections within the process. Suitable heating media are gases, vapors or liquids, preferably vaporous or liquid technical heat carrier media such as, for example, water, heat carriers based on mineral oil, or synthetic heat carriers (e.g. Diphyl™ Marlotherm®). Particularly preferred heating media are water or steam.

Preferably, all or part of the heat of condensation obtained by condensation in the condenser(s) of the further reaction column(s), preferably of the second reaction column, is used directly or indirectly for separating the dialkyl carbonate used in the reaction from the reaction alcohol.

Particularly preferably, all or part of the heat of condensation obtained by condensation in the condenser(s) of the further reaction column(s), preferably of the second reaction column, and/or in the intermediate condenser(s) of the first reaction column that is/are optionally present is used directly or indirectly for separating the dialkyl carbonate from the alkyl alcohol formed during the reaction.

Also preferably, the heat of condensation obtained by condensation in the condenser(s) of the further reaction column(s), preferably of the second reaction column, and/or in the intermediate condenser(s) of the first reaction column that is/are optionally present is used directly or indirectly, partly for separating the dialkyl carbonate from the alkyl alcohol formed during the reaction and partly for evaporating the dialkyl carbonate introduced into the first reaction column.

Particularly preferably, all or part of the heat of condensation obtained by condensation in the intermediate condenser(s) of the first reaction column that is/are optionally present is used directly or indirectly for evaporating the dialkyl carbonate introduced into the first reaction column.

In preferred embodiments of the process according to the invention, all or part of the heat of condensation obtained by condensation in the intermediate condenser(s) of the first reaction column is used directly or indirectly for evaporating the dialkyl carbonate introduced into the first reaction column, and all or part of the heat of condensation obtained by condensation in the condenser(s) of the further reaction column(s) is used directly or indirectly for separating the dialkyl carbonate from the alkyl alcohol formed during the reaction.

In the process according to the invention, streams of alkyl alcohol formed during the reaction (reaction alcohol) and also of unreacted dialkyl carbonate or dialkyl carbonate formed during the reaction are obtained in the transesterification and/or disproportionation in the first transesterification column and/or the further reaction column(s), and these streams are preferably removed in one or more streams in admixture. According to the invention, all or part of the dialkyl carbonate that has not reacted in the reaction columns or that has formed during the reaction is separated from the alkyl alcohol formed during the reaction (reaction alcohol) in at least one further process step comprising at least one distillation column. Preferably, at least one stream containing unreacted dialkyl carbonate or dialkyl carbonate formed during the reaction and alkyl alcohol formed during the reaction is removed at the top of the first reaction column and fed for separation to at least one further process step comprising at least one distillation column.

Preferably, after condensation at the top of the first reaction column, all or part of the vapor mixture removed at the top of the first reaction column, which vapor mixture contains dialkyl carbonate and alkyl alcohol formed during the reaction, is fed to at least one further process step comprising at least one distillation column for separation of dialkyl carbonate and alkyl alcohol.

Separation of the dialkyl carbonate and the reaction alcohol is preferably carried out by distillation in one or more distillation columns or in a combination of distillation and membrane separation—referred to as the hybrid process herein below.

If the reaction alcohol and the dialkyl carbonate form an azeotropic mixture (e.g. methanol and dimethyl carbonate), an at least two-stage process, such as, for example, a two-pressure process, an extractive distillation, a heteroazeotropic distillation with a low-boiling entrainer, or a hybrid process, is preferably used. The two-pressure process or a hybrid process is particularly preferably used. The two-pressure process is very particularly preferably used. Such processes are known in principle to the person skilled in the art (see e.g. Ullmann's Encyclopedia of Industrial Chemistry, Vol. 7, 2007, Chap. 6.4. and 6.5.; Chemie Ingenieur Technik (67) Nov. 1995).

If the reaction alcohol and the dialkyl carbonate do not form an azeotropic mixture (e.g. ethanol and diethyl carbonate), the separation is preferably carried out in a single distillation column.

If the reaction alcohol and the dialkyl carbonate form an azeotropic mixture, the distillate of a first distillation column of the process step for separating dialkyl carbonate and alkyl alcohol (reaction alcohol) preferably exhibits an almost azeotropic composition. In this case, this is preferably fed in a two-pressure process to at least one further distillation column which is operated at an operating pressure below that of the first distillation column. Owing to the difference in the operating pressure, the composition of the azeotropic mixture is shifted to lower contents of reaction alcohol. There is obtained as the bottom product of this second or further distillation column(s) reaction alcohol having a purity of from 90 to 100 wt. %, based on the total weight of the isolated bottom product, and as distillate an almost azeotropic mixture. In very particularly preferred embodiments, the second or further distillation column(s) operating at a lower operating pressure is/are preferably operated with the heat of condensation of the top condenser(s) of the first distillation column.

In the two-pressure process, the pressure dependence of the azeotropic composition of a two-component mixture is utilized. In the case of a mixture of reaction alcohol (alkyl alcohol) and dialkyl carbonate, such as, for example, methanol and dimethyl carbonate, the azeotropic mixture is shifted to higher reaction alcohol contents as the pressure increases. If a mixture of these two components is fed to a column (dialkyl carbonate column), the reaction alcohol content being below the corresponding azeotropic composition for the operating pressure of this column, there is obtained as distillate a mixture having an almost azeotropic composition and as bottom product almost pure dialkyl carbonate. The azeotropic mixture so obtained is fed to a further distillation column. (alkyl alcohol column). This operates at a lower operating pressure as compared with the dialkyl carbonate column. As a result, the position of the azeotropic mixture is shifted to lower reaction alcohol contents. As a result, it is possible to separate the azeotropic mixture obtained in the dialkyl carbonate column into a distillate of almost azeotropic composition and almost pure reaction alcohol. The distillate of the alkyl alcohol column is fed to the dialkyl carbonate column again at a suitable location.

The operating pressure of the alkyl alcohol column is preferably so chosen that the column can be operated with the waste heat of the dialkyl carbonate column. The operating pressure is from 0.1 to 1 bar, preferably from 0.3 to 1 bar. The operating pressure of the dialkyl carbonate column is in the range from 1 to 50 bar, preferably from 2 to 20 bar.

Figure 3:
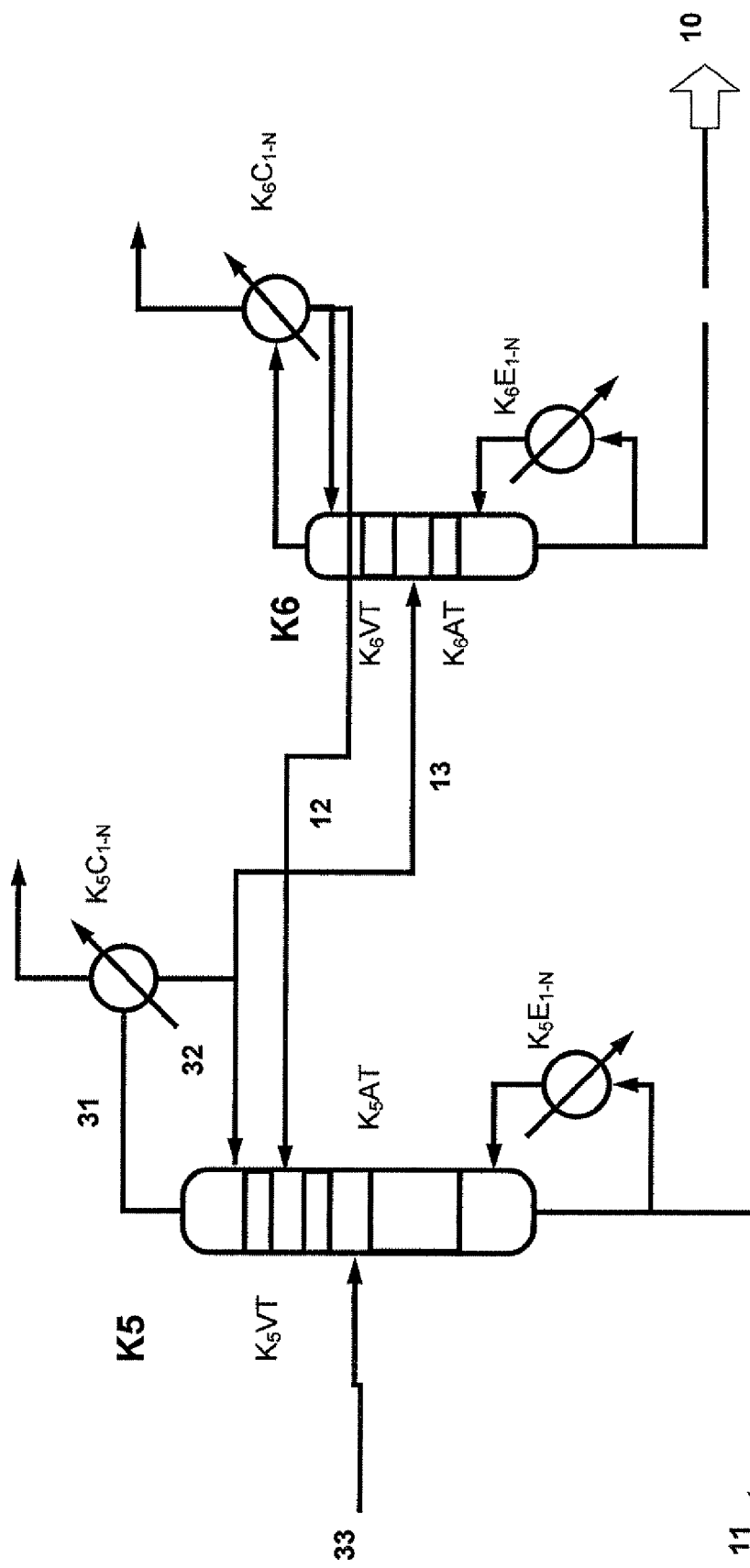
FIG. 3 is a schematic representation of an embodiment of a separation of dialkyl carbonate and reaction alcohol suitable for use in various embodiments of the invention.

An example of a reaction procedure in the separation of dialkyl carbonate and reaction alcohol by the two-pressure process is shown in FIG. 3.

A further preferred process for separating azeotropic mixtures of reaction alcohol and dialkyl carbonate is the hybrid process. In the hybrid process, the separation of a two-component mixture is carried out by means of a combination of distillation and membrane processes. Use is made of the fact that the components can be separated from one another at least partly by means of membranes on the basis of their polar properties and their different molecular weights. In the case of a mixture of reaction alcohol and dialkyl carbonate, such as, for example, methanol and dimethyl carbonate, pervaporation or vapor permeation using suitable membranes yields as the permeate a mixture that is rich in reaction alcohol and as the retentate a mixture that is low in reaction alcohol. If a mixture of these two components is fed to a column (dialkyl carbonate column), the reaction alcohol content being below the corresponding azeotropic composition for the operating pressure of this column, a mixture having a markedly increased reaction alcohol content as compared with the feed stream is obtained as the distillate and almost pure dialkyl carbonate is obtained as the bottom product.

In the case of a hybrid process of distillation and vapor permeation, the distillate is removed from the column in vapor form. The vaporous mixture so obtained is fed to a vapor permeation, optionally after superheating. The vapor permeation is so carried out that almost the operating pressure of the column is established on the retentate side and a lower pressure is established on the permeate side. The operating pressure of the column is in the range from 1 to 50 bar, preferably from 1 to 20 bar and particularly preferably from 2 to 10 bar. The pressure on the permeate side is from 0.05 to 2 bar. There is thereby obtained on the permeate side a fraction that is rich in reaction alcohol, with a reaction alcohol content of at least 70 wt. %, preferably at least 90 wt. %, based on the total weight of the fraction. The retentate, which has a reduced reaction alcohol content as compared with the distillate of the column, is optionally condensed and fed to the distillation column again.

In the case of a hybrid process of distillation and pervaporation, the distillate is removed from the column in liquid form. The mixture so obtained is fed to pervaporation, optionally after heating. The pervaporation is so carried out that the operating pressure on the retentate side is identical with or increased as compared with the column and a lower pressure is established on the permeate side. The operating pressure of the column is in the range from 1 to 50 bar, preferably from 1 to 20 bar and particularly preferably from 2 to 10 bar. The pressure on the permeate side is from 0.05 to 2 bar. There is thereby obtained on the permeate side a vaporous fraction that is rich in reaction alcohol, with a reaction alcohol content of at least 70 wt. %, preferably at least 90 wt. %, based on the total weight of the fraction. The liquid retentate, which has a reduced reaction alcohol content as compared with the distillate of the column, is fed to the distillation column again. Owing to the evaporation of the permeate, heat is required, which may not be present to a sufficient degree in the feed stream to the pervaporation. A membrane separation by means of pervaporation can therefore optionally be heated by additional heat exchangers, these being integrated or optionally arranged between a plurality of series-connected pervaporation steps.

In the case of a hybrid process, the separation of dialkyl carbonate and reaction alcohol particularly preferably takes place by means of a combination of distillation and vapor permeation.

Figure 4:
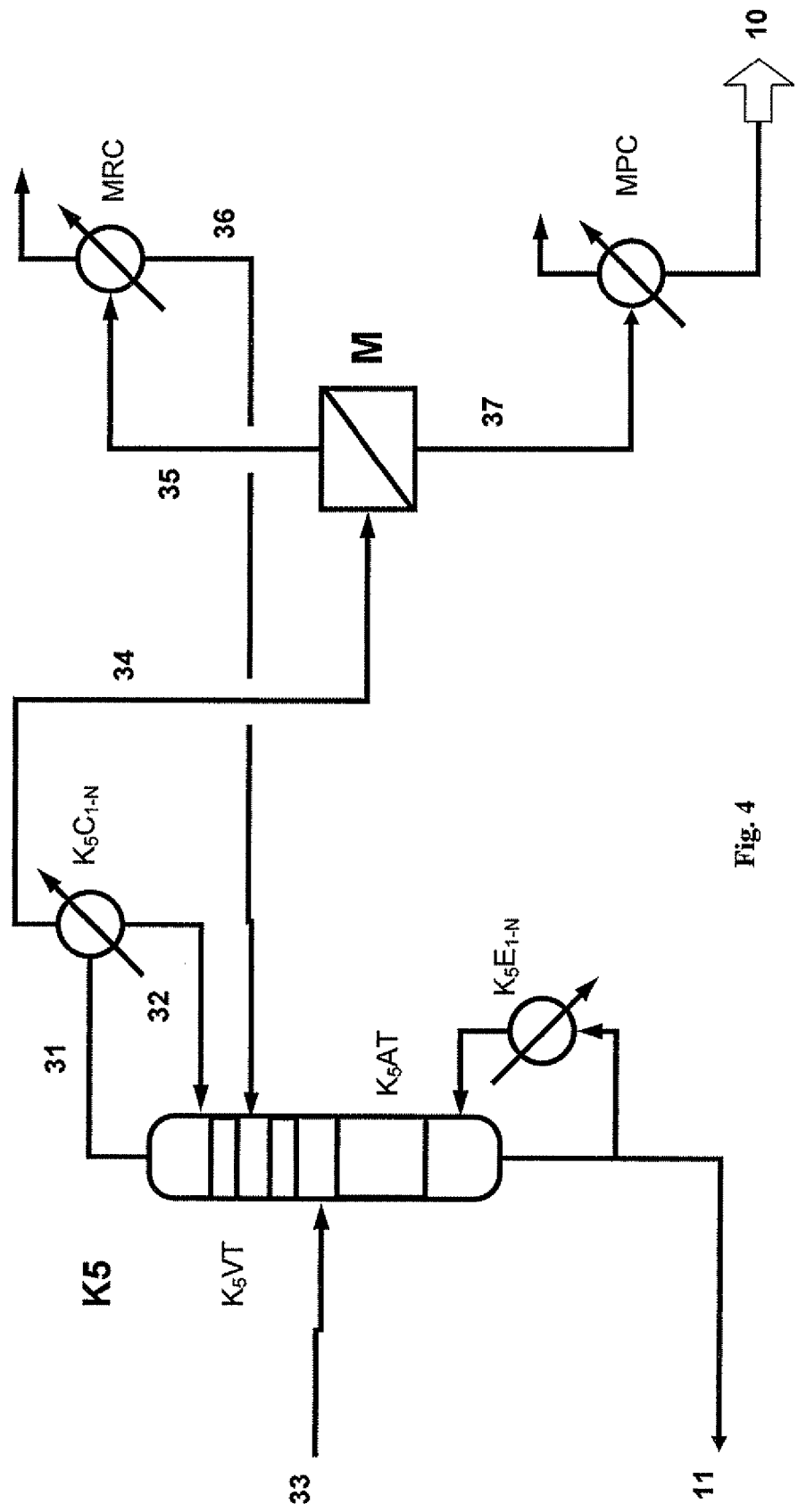
FIG. 4 is a schematic representation of another embodiment of a separation of dialkyl carbonate and reaction alcohol suitable for use in various embodiments of the invention.

An exemplary embodiment of the separation of dialkyl carbonate and reaction alcohol according to the hybrid process by means of vapor permeation is shown in FIG. 4.

Irrespective of the chosen process for separating dialkyl carbonate and reaction alcohol, the process conditions, such as pressure and temperature, are advantageously so chosen that the heat of condensation obtained by condensation in the condenser(s) of the further reaction column(s) and/or in the intermediate condenser(s) of the first reaction column that is/are optionally present can be used effectively.

To this end, the operating pressure, and accordingly also the operating temperature, in the distillation column(s) of the process step for separating dialkyl carbonate and alkyl alcohol is so adjusted that the distillation column(s) can be operated wholly or partially with the heat of condensation in the condenser(s) of the further reaction column(s) and/or in the intermediate condenser(s) of the first reaction column that is/are optionally present. To this end, the operating pressure in the distillation column(s) of the process step for separating dialkyl carbonate and alkyl alcohol is preferably so adjusted that the evaporation temperature in the bottom of the distillation column(s) of the process step for separating dialkyl carbonate and alkyl alcohol is below the condensation temperature in the condenser(s) of the further reaction column(s) and/or in the intermediate condenser(s) of the first reaction column that is/are optionally present.

The heat required for the separation of reaction alcohol and dialkyl carbonate is supplied at a temperature of from 100 to 300° C., preferably from 100 to 230° C. and particularly preferably from 120 to 200° C. In order to permit efficient heat integration with the intermediate condenser of the first reaction column or with the condensers of the second reaction column, the condensation in the condenser(s) of the further reaction column(s) and/or in the intermediate condenser(s) of the first reaction column that is/are optionally present is carried out at a temperature that is increased by from 1 to 100° C., preferably from 2 to 50° C. and particularly preferably from 5 to 40° C., All or part of the heat of condensation from the condenser(s) of the further reaction column(s) and/or from the intermediate condenser(s) of the first reaction column that is/are optionally present can be used, for example, for preheating feed streams to the distillation column(s) and/or for heating one or more column sections. In preferred embodiments, the heat of condensation from the condenser(s) of the further reaction column(s) and/or from the intermediate condenser(s) of the first reaction column that is/are optionally present is used partly for preheating the feed stream(s) to the distillation column(s) of the process step for separating dialkyl carbonate and alkyl alcohol and partly for evaporating the bottom in the distillation column(s). In a very preferred embodiment of the process according to the invention, in which a cascade of at least two, preferably three, top condensers is used at the top of the second reaction column, the heat of condensation from the first condenser of this cascade is used for evaporating the bottom product of the or of the first distillation column of the process step for separating dialkyl carbonate and alkyl alcohol, and the heat of condensation from the second condenser of the cascade is used for preheating the feed stream to the or to the first distillation column of the process step for separating dialkyl carbonate and alkyl alcohol.

The distillation column(s) preferably has/have a rectifying section having from 5 to 40 theoretical stages for concentrating the reaction alcohol, and a stripping section having from 5 to 40 theoretical stages for concentrating the dialkyl carbonate.

The process according to the invention is preferably carried out continuously.

By using the heat of condensation from the condenser(s) of the further reaction column(s) and optionally from the intermediate condensers of the first reaction column, the separation of the reaction alcohol from excess dialkyl carbonate can be carried out with a markedly reduced energy consumption. The cooling capacity in the transesterification steps can thereby be reduced to an equal degree. A substantial advantage of the process according to the invention as compared with the processes of the prior art is, therefore, the marked reduction in energy consumption in the preparation of diaryl carbonates or alkylaryl carbonates. At the same time, the process can be carried out with a simple outlay in terms of apparatus because, owing to the use of column arrangements, a complicated reactor arrangement with a plurality of separate series-connected reaction zones is not required.

Part of a process according to the invention is explained by reference to FIG. 1. FIG. 1 shows a process according to the invention without any subsequent steps such as additional reaction steps or additional purification in any further columns.

FIG. 1 describes a first transesterification step employing reactive rectification in a first reaction column having an intermediate condenser in general, a second reaction step for the transesterification or disproportionation of alkylaryl carbonate in a second reaction column, and the separation of the mixture obtained as top product in the first reaction column and containing dialkyl carbonate and reaction alcohol in a further process step comprising at least one distillation column.

Figure 2:
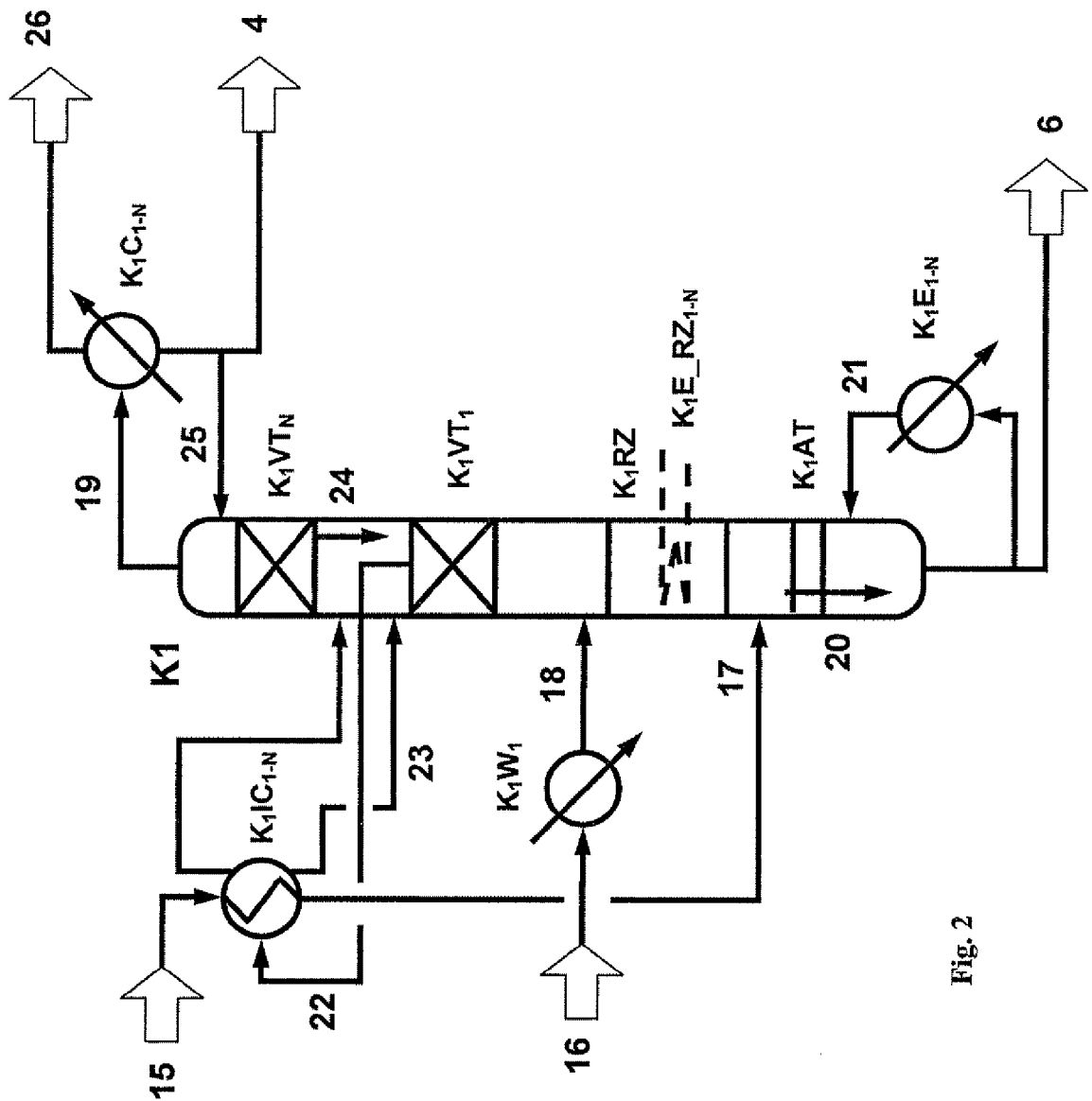
FIG. 2 is a schematic representation of an embodiment of a first reaction column suitable for use in various embodiments of the invention.

FIG. 2 describes a particularly preferred embodiment of a first reaction column (reactive rectification column) having an external arrangement of an intermediate condenser and combination with the evaporation of the dialkyl carbonate for feeding back the resulting heat of condensation.

FIG. 3 describes a preferred embodiment of the separation of dialkyl carbonate and reaction alcohol by the two-pressure process.

FIG. 4 describes a preferred embodiment of the separation of dialkyl carbonate and reaction alcohol by the hybrid process.

The figures serve to explain the invention by way of example and are not to be regarded as limiting.

In FIGS. 1 to 4, the abbreviations have the following meanings:

K1 alkylaryl carbonate reaction column (AAC reaction column, first reaction column)
$K_1C_{1-N}$ condenser(s) 1-N of the AAC reaction column
$K_1E_{1-N}$ evaporators 1-N of the AAC reaction column
$K_1IC_{1-N}$ intermediate condenser(s) 1 to N of the AAC reaction column
$K_1VT_1$ lower rectifying section of the AAC reaction column
$K_1VT_N$ upper rectifying section of the AAC reaction column
$K_1W_1$ preheater/evaporator/superheater for dialkyl-carbonate-containing stream
$K_1W_2$ preheater/evaporator for starting material stream with aromatic hydroxy compound
$K_1RZ$ reaction zone of the AAC reaction column $K_1E\_RZ_{1-N}$ intermediate evaporators 1 to N in the region of the reaction zone of the AAC reaction column K2 diaryl carbonate reaction column (Dac Reaction Column/Second Reaction Column)

$K_2C_{1-N}$ condenser(s) 1 to N of the DAC reaction column $K_2E_{1-N}$ evaporators 1 to N of the DAC reaction column $K_2VT$ rectifying section of the DAC reaction column $K_2AT$ stripping section & reaction zone of the DAC reaction column $K_2E\_AT_{1-N}$ intermediate evaporators in the stripping section of the 2nd reaction column K5 dialkyl carbonate distillation column (DAK)

$K_5VT$ rectifying section of the DAK $K_5AT$ stripping section of the DAK $K_5W_1$ preheater/evaporator for stream containing reaction alcohol and dialkyl carbonate $K_5C_{1-N}$ condenser(s) 1 to N of the DAK $K_5C_{1-N}$ evaporators 1 to N of the DAK $K_5E\_AT_{1-N}$ intermediate evaporators in the stripping section of the DAK K6 reaction alcohol distillation column (RAK)

$K_6C_{1-N}$ condenser(s) 1 to N of the RAK $K_6E_{1-N}$ evaporators 1 to N of the RAK $K_6VT$ rectifying section of the RAK $K_6AT$ stripping section of the RAK M membrane separation (vapor permeation or pervaporation)

MRC condenser for retentate after membrane separation

MPC condenser for permeate after membrane separation

The following material streams are also mentioned in FIGS. 1 to 4:

1 starting material feed stream containing dialkyl carbonate
2 starting material feed stream containing aromatic hydroxy compound
3 distillate of the second reaction column
4 distillate of the first reaction column
5 stream containing dialkyl carbonate and reaction alcohol
6 bottom product of the first reaction column
7 intermediate-boiler purge
8 bottom product of the second reaction column
9 stream containing alkylaryl carbonate and aromatic hydroxy compound
10 reaction alcohol discharge
11 dialkyl-carbonate-containing stream from dialkyl carbonate distillation column (K5)
12 distillate of the reaction alcohol distillation column
13 distillate of the dialkyl carbonate distillation column
14 stream containing dialkyl carbonate and reaction alcohol
15 dialkyl-carbonate-containing stream to the first reaction column
16 stream containing aromatic hydroxy compound to the first reaction column
17 dialkyl-carbonate-containing stream after evaporation
18 stream with aromatic hydroxy compound after heating
19 vapor stream at the top of the first reaction column
20 liquid discharge from the stripping section of the first reaction column
21 vapor/liquid mixture from the bottom evaporator of the first reaction column
22 vapor mixture from the lower rectifying section of the first reaction column
23 condensate of the intermediate condenser(s) of the first reaction column
24 liquid mixture discharge from the upper rectifying section of the first reaction column
25 reflux of the first reaction column
26 residual vapor mixture from condensation of the first reaction column
27 vapor stream at the top of the second reaction column
28 liquid mixture discharge from the reaction zone or optional stripping section of the second reaction column
29 vapor/liquid mixture from the bottom evaporator of the second reaction column
30 reflux of the second reaction column
31 vapor stream at the top of the distillation column (K5)
32 reflux of the distillation column (K5)
33 feed mixture to the distillation column (K5)
34 distillate of the distillation column to membrane separation (M)
35 retentate membrane separation (M) to the condenser (MRC)
36 liquid retentate to the distillation column (K5)
37 permeate of the membrane separation (M) to the condenser (MPC).

FIG. 1 shows inter alia a first reaction column K1 into which the two starting material streams, that is to say a stream 16 containing the aromatic hydroxy compound and a stream 15 containing the dialkyl carbonate, are guided countercurrently within a countercurrent esterification in the region of a reaction zone RZ and are reacted to form alkylaryl carbonates and small amounts of diaryl carbonates.

In the case of continuous processes in particular, the stream 15 containing the dialkyl carbonate can also contain, in addition to the dialkyl carbonate, portions of the aromatic hydroxy compound, the aliphatic hydroxy compound $R^1$—OH and/or $R^2$—OH obtained in the reaction (reaction alcohol), very small amounts of the alkylaryl carbonate and/or diaryl carbonate obtained in the transesterification, and undesirable by-products formed in the reaction. The stream 15 containing the dialkyl carbonate can contain, for example, from 0 to 5 wt. %, preferably from 0.05 to 3 wt. % and particularly preferably from 0.05 to 2 wt. %, of the reaction alcohol, from 0 to 40 wt. %, preferably from 0 to 10 wt. %, particularly preferably from 0 to 5 wt. %, of the aromatic hydroxy compound, from 0 to 5 wt. % alkylaryl carbonate, from 0 to 5 wt. % diaryl carbonate and from 0 to 5 wt. % of other by-products formed in the reaction (e.g. alkyl aryl ethers) or impurities already contained in the starting materials, in each case based on the total weight of the dialkyl-carbonate-containing stream. The stream 15 containing the dialkyl carbonate preferably contains from 50 to 100 wt. % dialkyl carbonate, based on the total weight of the dialkyl-carbonate-containing stream, the sum of the individual components mentioned above being 100 wt. %. In continuous processes in particular, the stream 16 containing the aromatic hydroxy compound can also contain, in addition to the aromatic hydroxy compound, portions of the dialkyl carbonate, the alkylaryl carbonate and/or diaryl carbonate formed in the transesterification, very small amounts of the reaction alcohol and undesirable by-products obtained in the reaction. For example, the content of the dialkyl carbonate can be from 0 to 50 wt. %, the content of the reaction alcohol from 0 to 10 wt. %, preferably from 0 to 5 wt. %, the content of the alkylaryl carbonate and of the diaryl carbonate in each case from 0 to 10 wt. %, preferably from 0 to 5 wt. %, and the content of undesirable by-products from 0 to 5 wt. %, preferably from 0 to 1 wt. %, in each case based on the total weight of the stream containing the aromatic hydroxy compound. The catalyst can additionally be fed into the reaction column with the stream 16 containing the aromatic hydroxy compound. In that case, the content of catalyst is preferably from 0 to 5 wt. %, based on the total weight of the stream containing the aromatic hydroxy compound. Preferably, the stream 16 containing the aromatic hydroxy compound contains from 50 to 100 wt. % aromatic hydroxy compound, based on the total weight of the stream containing the aromatic hydroxy compound, the sum of the amounts of the individual components mentioned above being 100 wt. %.

Before it is introduced into the column K1, the stream 15 containing the dialkyl carbonate is evaporated partially or completely and optionally superheated. The stream 16 containing the aromatic hydroxy compound is heated before it is introduced into the column K1 and is thereby optionally partially evaporated. The starting material streams 17 and 18, after evaporation and optional superheating and after heating, respectively, are guided countercurrently to one another in the reaction zone RZ that is to say the stream 18 containing the aromatic hydroxy compound is fed in at the top end of the reaction zone RZ in heated, predominantly liquid form, and the stream 17 containing the dialkyl carbonate is fed in, predominantly in gaseous or optionally slightly superheated form, at the bottom end of the reaction zone. The aliphatic hydroxy compound $R^1$—OH and/or $R^2$—OH obtained in the reaction is drawn off in vapor form (19) at the top of the column, together with unreacted dialkyl carbonate, and the less readily volatile alkylaryl carbonate is removed at the foot of the column K1 (6) in the form of a liquid stream together with unreacted amounts of the aromatic hydroxy compound, diaryl carbonate and optionally further not readily volatile compounds. The energy required to establish the desired temperature profile can be effected inter alia at the bottom of the column by one or more evaporators $K_1E_{1-N}$. To that end, the liquid mixture (20) flowing from the stripping section $K_1AT$, or, if a stripping section is not present, from the reaction zone $K_1RZ$, is partially evaporated. Depending on the design of the evaporator, only vapor or a vapor/liquid mixture (stream 21) is obtained at the outlet of the evaporator. The vapor contained in the stream 21 is fed to the stripping section ($K_1AT$) from beneath or, if a stripping section is not present, is fed to the reaction zone $K_1RZ$ from beneath. Heat can be supplied in the region of the reaction zone by additional intermediate evaporators $K_1E\_RZ_{1-N}$. In the stripping section $K_1AT$ provided between the reaction zone $K_1RZ$ and the evaporators $K_1E_{1-N}$, concentration of the resulting alkylaryl carbonate and of the diaryl carbonate takes place, the disproportionation reaction of alkylaryl carbonate to diaryl carbonate already beginning to an enhanced degree in this portion of the column K1 owing to the depletion of dialkyl carbonate.

Concentration of the aliphatic hydroxy compound formed in the reaction (reaction alcohol) and of the excess dialkyl carbonate takes place in one or more rectifying section(s) located between the condenser(s) $K_1C_{1-N}$ and the reaction zone $K_1RZ$. During this concentration, a content of aromatic hydroxy compound(s) in the distillate 4 of from 0 to 40 wt. %, preferably from 0 to 10 wt. %, particularly preferably from 0 to 5 wt. %, based on the total weight of the distillate 4, is to be established. The rectifying section is divided into at least two sections, the upper and the lower rectifying sections, one or more intermediate condenser(s) $K_1IC_{1-N}$, preferably at least one intermediate condenser $K_1IC_1$, being located between the upper rectifying section $K_1VT_N$ and the lower rectifying section $K_1VT_1$. The intermediate condenser(s) $K_1IC_{1-N}$, or the intermediate condenser $K_1IC_1$, condensers) a portion of the vapors 22 rising from the lower rectifying section $K_1VT_1$. The vaporous mixture 22 entering the intermediate condenser(s) $K_1IC_{1-N}$, preferably at least one intermediate condenser $K_1IC_1$, preferably contains from 10 to 80 wt. % aromatic hydroxy compound. The condensation temperature in the intermediate condenser(s) $K_1IC_{1-N}$ is therefore markedly higher as compared with the condensation temperature in the top condenser $K_1C_{1-N}$ (N: condenser is optionally multi-stage), owing to the comparatively larger amounts of aromatic hydroxy compound. Depending on the operating pressure and the position of the concentration profile, the condensation temperature in the intermediate condenser(s) can preferably be in the range from 100 to 300° C., particularly preferably from 120 to 250° C., most particularly preferably from 150 to 240° C., and in the top condenser preferably in the range from 0 to 250° C., particularly preferably from 40 to 200° C. The condensate 23 formed in the intermediate condenser(s) $K_1IC_{1-N}$ and the liquid 24 flowing from the upper rectifying section $K_1VT_N$ located above it are guided onto the lower rectifying section $K_1VT_1$. The vaporous mixture downstream of the intermediate condenser(s) passes into the upper rectifying section $K_1VT_N$. The vapor 19 coming from the upper rectifying section $K_1VT_N$ is condensed to the greatest possible extent in the condenser(s) $K_1C_{1-N}$, part of the condensate being fed back to the upper rectifying section $K_1VT_N$ again as reflux (25) and part being removed as distillate stream 4. The distillate stream 4 contains substantially the dialkyl carbonate used in excess and the corresponding alkyl alcohol $R^1$—OH and/or $R^2$—OH formed in the reaction (reaction alcohol), and optionally small amounts of the aromatic hydroxy compound. The residual vapor mixture from the condenser(s) $K_1C_{1-N}$ is removed as vapor stream 26.

The heat of condensation liberated in the intermediate condenser(s) $K_1IC_{1-N}$, preferably at least the intermediate condenser $K_1IC_1$, can be fed directly or indirectly back into the process again as described above for the process according to the invention (not shown in FIG. 1).

In a preferred embodiment of the process according to the invention, the heat of condensation obtained in the intermediate condenser(s) $K_1IC_{1-N}$, preferably at least the intermediate condenser $K_1IC_1$, is used for heating a heat carrier medium. This is in turn used for evaporating and superheating the dialkyl-carbonate-containing stream 15 used in the countercurrent esterification in the reaction column K1. This preferred embodiment is an indirect use of the heat of condensation.

Another preferred embodiment of the transesterification in the first reaction column in the presence of at least one intermediate condenser is shown in FIG. 2. The intermediate condenser(s) is/are here arranged outside the first reaction column. Heating, evaporation and optionally superheating of the dialkyl-carbonate-containing stream 15 likewise take place in the intermediate condenser. The vaporous mixture 22 of the lower rectifying section $K_1VT_1$ is guided to the intermediate condenser(s) $K_1IC_{1-N}$, preferably to at least one intermediate condenser $K_1IC_1$, where it partially condenses. The condensate 23 obtained thereby is fed to the lower rectifying section $K_1VT_1$ again, and the uncondensed vapors are guided into the upper rectifying section $K_1VT_N$. Otherwise, the process shown in FIG. 2 corresponds to that shown in FIG. 1. The explanations given hereinbefore for FIG. 1 therefore apply analogously.

According to FIG. 1, the bottom product 6 of the first reaction column K1 is fed to a second reaction column K2. This can contain from 0 to 60 wt. % diaryl carbonate, from 5 to 80 wt. % alkylaryl carbonate, from 5 to 95 wt. % of the aromatic hydroxy compound, from 1 to 80 wt. % dialkyl carbonate, from 0 to 5 wt. % catalyst and from 0 to 5 wt. % of other by-products formed in the reaction (e.g. alkyl aryl ethers) or impurities already contained in the starting materials, in each case based on the total weight of the bottom product stream 6. Percentages are based on the total weight of the bottom product stream 6, the sum of the amounts of the individual components mentioned above being 100 wt. %.

In addition to the bottom product of the first reaction column, at least one further alkylaryl-carbonate-containing stream 9 can also be fed to the second reaction column. This stream 9 can come, for example, from a further refinery step for purification of the diaryl carbonate, such as, for example, a distillation column.

It can contain from 0 to 10 wt. % diaryl carbonate, from 10 to 100 wt. % alkylaryl carbonate, from 0 to 90 wt. % of the aromatic hydroxy compound, from 0 to 20 wt. % dialkyl carbonate and from 0 to 20 wt. % of other by-products obtained in the reaction (e.g. alkyl aryl ethers) or impurities already contained in the starting materials, in each case based on the total weight of the dialkyl-carbonate-containing stream. Percentages are based on the total weight of the stream 9, the sum of the amounts of the individual components mentioned above being 100 wt. %.

Streams 6 and 9 are fed to the reaction zone $K_2AT$ of the second reaction column.

The reaction alcohol $R^1$—OH and/or $R^2$—OH obtained in the transesterification is removed in vapor form at the top of column K2 (27) together with unreacted dialkyl carbonate or dialkyl carbonate freed in the disproportionation, and unreacted aromatic hydroxy compound, and the less readily volatile diaryl carbonate is removed as a liquid stream at the bottom of the second reaction column K2 (8) together with unreacted amounts of the aromatic hydroxy compound, alkylaryl carbonate and optionally further not readily volatile compounds.

The energy required to establish the desired temperature profile can be effected inter alia at the bottom of the column by one or more evaporators $K_2E_{1-N}$. To this end, the liquid mixture (28) flowing out of the reaction zone is partially evaporated. Depending on the design of the evaporator, only vapor or a vapor/liquid mixture (stream 29) is obtained at the outlet of the evaporator. The vapor contained in the stream 29 is fed from beneath to the stripping section ($K_2AT$), which at the same time also serves as the reaction zone and consists of a plurality of sections. Heat can be supplied in the region of the reaction zone by additional intermediate evaporators $K_2E\_AT_{1-N}$. Roth the reaction (transesterification and/or preferably disproportionation) and the separation of the resulting low-boiling reaction products (reaction alcohol and dialkyl carbonate) and the aromatic hydroxy compound take place in the reaction zone $K_2AT$ and in the evaporator $K_2E_{1-N}$.

In a rectifying section $K_2VT$ located between the condenser(s) $K_2C_{1-N}$ and the reaction zone $K_2AT$, the content of high-boiling compounds such as, for example, alkylaryl carbonate or diaryl carbonate is reduced. A content of alkylaryl carbonate in the distillate 3 of from 0 to 20 wt. %, preferably from 0 to 5 wt. %, particularly preferably from 0 to 2 wt. %, based on the total weight of the distillate 3, is preferably established thereby. The rectifying section can be constructed analogously to the first reaction column with one or more intermediate condensers. In the preferred embodiment shown in FIG. 2, however, the rectifying section of K2 is constructed without intermediate condenser(s).

The condenser(s) $K_2C_{1-N}$, in a very particularly preferred embodiment a cascade of condensers, at the top of K2 condense a portion of the vapors 27 rising from the rectifying section $K_2VT$. The vaporous mixture 27 entering the condenser(s) $K_2C_{1-N}$ preferably contains from 10 to 90 wt. % aromatic hydroxy compound. The condensation temperature in the condenser(s) $K_2C_{1-N}$ is therefore high owing to comparatively large amounts of aromatic hydroxy compound. Depending on the operating pressure and composition of the vaporous mixture 27, the condensation temperature in the condenser(s) can preferably be in the range from 100 to 300° C., particularly preferably from 120 to 250° C., very particularly preferably from 150 to 240° C. The condensate is partly fed to the rectifying section $K_2VT$ again as reflux 30 and partly removed as distillate stream 3.

The distillate stream 3 substantially contains aromatic hydroxy compounds and small amounts of reaction alcohol, preferably from 0 to 5 wt. %.

The distillate of the first reaction column (4), optionally together with further streams containing reaction alcohol and dialkyl carbonate (5 and/or 12), optionally after heating and/or partial evaporation, is fed to a distillation column K5 (dialkyl carbonate distillation column) for separation of the dialkyl carbonate from the reaction alcohol that has formed, the resulting dialkyl-carbonate-containing stream 11 being fed to the dialkyl-carbonate-containing feed stream 15 of the first reaction column again and the reaction alcohol that is separated off being discharged from the process (10). Stream 5 can come, for example, from further purification or by-product separation steps.

If the reaction alcohol and the dialkyl carbonate form an azeotropic mixture, an approximately azeotropic mixture is preferably obtained as the distillate (13) of the distillation column K5. At least one further separation step is therefore necessary for complete separation of the reaction alcohol and the dialkyl carbonate.

If the reaction alcohol and the dialkyl carbonate do not form an azeotropic mixture, there is obtained as the distillate preferably reaction alcohol with a content of from 95 to 100 wt. %.

A mixture containing dialkyl carbonate with less than 5 wt. % reaction alcohol is removed as the bottom product of the distillation column K5.

The dialkyl carbonate distillation column K5 has a rectifying section with preferably from 5 to 40 theoretical stages for concentration of the reaction alcohol, and a stripping section with preferably from 5 to 40 theoretical stages for concentration of the dialkyl carbonate.

The energy required for the distillation in the dialkyl carbonate distillation column can be effected inter alia at the bottom of the column by one or more evaporators $K_5E_{1-N}$. Heat can be supplied in the region of the stripping section $K_5AT$ by additional intermediate evaporators $K_5E\_AT_{1-N}$.

The condenser(s) $K_5C_{1-N}$ condense the vapors 31 rising from the rectifying section $K_5VT$. The condensate is partly fed to the rectifying section $K_5VT$ again as reflux 32 and partly removed as distillate stream 13.

The distillate stream 13 contains reaction alcohol and dialkyl carbonate in almost azeotropic composition. If the reaction alcohol and the dialkyl carbonate do not form an azeotropic mixture, almost pure reaction alcohol is obtained as the distillate.

The operating pressure in the dialkyl carbonate distillation column (K5) is so adjusted that the column can be operated with waste heat from the transesterification process. The heat of condensation from the intermediate condenser of the first reaction column and/or from the condenser(s) of the second reaction column is preferably used for this purpose. The operating pressure in column K5 is preferably so adjusted that the evaporation temperature in the bottom of column K5 is below the condensation temperature in the intermediate condenser of the first reaction column and/or in the condenser(s) of the second reaction column.

If the reaction alcohol and the dialkyl carbonate form an azeotropic mixture under the conditions in the distillation column K5, this can be separated by means of entrainer or extractive rectification, by the two-pressure process or by means of a combination of rectification and membrane separation. The two-pressure process is particularly preferably used for separating the reaction alcohol and the dialkyl carbonate, and this is explained by way of example by means of FIGS. 1 and 3.

If the distillate of the distillation column K5 has an azeotropic composition, it is fed to a further column (reaction alcohol distillation column (RAK); K6 in FIGS. 1 and 3), which operates at an operating pressure below that of the distillation column K5. Owing to the differing operating pressures, the position of the azeotropic mixture is shifted to lower contents of reaction alcohol. A reaction alcohol having a purity of from 90 to 100 wt. % is obtained as the bottom product 10 of the distillation column K6, and an almost azeotropic mixture is obtained as the distillate of column K6. In a particularly preferred embodiment, column K6, which operates at a lower operating pressure, is operated with the heat of condensation of the top condenser(s) of column K5.

The reaction alcohol distillation column (RAK) K6 has a rectifying section $K_6VT$ with from 5 to 40 theoretical stages for concentrating the reaction alcohol, and a stripping section $K_6AT$ with from 5 to 40 theoretical stages for concentrating the dialkyl carbonate.

Also preferably, the azeotropic mixture of reaction alcohol and dialkyl carbonate can also be separated by means of a hybrid process in the form of a combination of rectification and membrane separation (see FIG. 4). In this process, the distillate of K5 is fed to a membrane separation M, the various forms of which have already been described hereinbefore. A fraction 37 that is rich in reaction alcohol and has a reaction alcohol content of at least 70 wt. %, preferably at least 90 wt. %, based on the total weight of the fraction, is obtained on the permeate side and is condensed in the condenser MPC. The retentate 35, which has a reduced reaction alcohol content as compared with the distillate of column K5, is condensed in the condenser MRC and preferably fed to the distillation column K5 again (36).

The invention will now be described in further detail with reference to the following non-limiting examples.

EXAMPLES

Example 1

According to the Invention

In a first reaction column comprising
an upper rectifying section ($K_1VT_2$) having 4 theoretical stages,
an intermediate condenser ($K_1IC_1$),
a lower rectifying section ($K_1VT_1$) having 4 theoretical stages,
a reaction zone ($K_1RZ$) having 30 reaction plates (hold-up: 12 l), 3 plates being equipped with heating elements ($K_1E\_RZ_{1-3}$), and
a stripping section $K_1AT$ having 6 plates (hold-up: 12 l), 400 kg/h of a mixture of 85.4 wt. % phenol, 9.2 wt. % dimethyl carbonate, 3.2 wt. % diphenyl carbonate, 1.5 wt. % titanium tetraphenolate, 0.3 wt. % anisole, 0.3 wt. % methylphenyl carbonate and 0.1 wt. % methanol are fed at the top end of the reaction zone. At the bottom end of the reaction zone, 539.6 kg/h of a vapor mixture, superheated by 5° C., of 98.8 wt. % dimethyl carbonate, 0.9 wt. % phenol, 0.2 wt. % anisole and 0.1 wt. % methanol are fed in.

456.9 kg/h of a product mixture consisting of 51 wt. % phenol, 27.3 wt. % MPC (124.7 kg/h), 11.9 wt. % DPC (54.3 kg/h), 8.1 wt. % DMC, 0.4 wt. % anisole and 1.3 wt. % titanium tetraphenolate are obtained at the bottom of the column.

The first reaction column is operated at a top pressure (above $K_1VT_2$) of 3.6 bar and a reflux ratio of 1.15. A temperature of 230° C. is established in the bottom of the column, and a mean reaction temperature of 215° C. is established in the reaction zone. A bottom evaporator $K_1E_1$ and intermediate evaporators $K_1E\_RZ_1$-$K_1E\_RZ_3$ in the reaction zone are operated with hot vapor at a vapor pressure of 35 bar, a thermosiphon reboiler being used as the bottom evaporator $K_1E_1$ and heating elements (steam) integrated in the reaction plates being used as intermediate evaporators. The inlet temperature into the intermediate condenser is 205° C., the outlet temperature is 193° C. and the cooling capacity is 57 kW. The heat of condensation formed in the intermediate condensation can be used to produce hot vapor having a hot vapor pressure of 8 bar (dewpoint: 170.4° C.). The heating capacity required for evaporation of the dimethyl-carbonate-containing stream is 52 kW. The evaporation and superheating of the dimethyl carbonate are carried out at a temperature of from 135 to 152° C., for which purpose the vapor used in the intermediate condenser can be used without difficulty.

The bottom product of the first reaction column is fed to a second reaction column comprising
a rectifying section ($K_2VT$) having 10 theoretical stages,
at the top end of the reaction zone a stripping section including a reaction zone ($K_2AT$) having 22 theoretical stages.

In addition, 81.9 kg/h of a mixture of 69.9 wt. % methylphenyl carbonate, 28.3 wt. % phenol, 1.2 wt. % dimethyl carbonate, 0.5 wt. % diphenyl ether and 0.1 wt. % diphenyl carbonate are fed to the bottom half of the stripping section ($K_2AT$).

236.6 kg/h of a product mixture comprising 62.8 wt. % diphenyl carbonate, 24.2 wt. % methylphenyl carbonate, 9.8 wt. % phenol, 0.4 wt. % DMC, 2.6 wt. % titanium tetraphenolate and 0.2 wt. % diphenyl ether are thereby obtained at the bottom of the second reaction column.

In addition, 238.2 kg/h of liquid distillate comprising 83.5 wt. % phenol, 15.5 wt. % dimethyl carbonate, 0.6 wt. % methylphenyl carbonate, 0.3 wt. % anisole and 0.1 wt. % methanol are removed.

The vapor mixture coming from the second reaction column is only partially condensed, so that 59.5 kg/h of a vaporous product stream are also removed after the condensation for the purpose of discharging middle-boiling by-products, in particular anisole. This vaporous product stream contains 59.8 wt. % dimethyl carbonate, 38.2 wt. % phenol, 1.6 wt. % methanol, 0.3 wt. % anisole and 0.1 wt. % methylphenyl carbonate.

The second reaction column is operated at a top pressure (above $K_2VT$) of 1 bar and a reflux ratio of 0.65. The pressure loss in the column is less than 50 mbar owing to the use of structured packing in the rectifying and stripping section. The mixture leaving the reaction zone has a temperature of 198° C. and is fed to a two-stage evaporation. The outlet temperature is 209° C. after the first evaporation stage and 230° C. after the second evaporation stage. The evaporator used is a thermosiphon reboiler in the first stage and a kettle-type evaporator in the second stage. The total evaporator capacity is 66.4 kW.

The condensation of the vapor mixture removed at the top of the second reaction column takes place in three stages, at from 174 to 165° C. in the first stage (46 kW), at from 165 to 155° C. in the second stage (17 kW) and at from 155 to 154° C. in the third stage (1 kW). The heat of condensation of the first and second stages is used for separating a mixture of dimethyl carbonate and methanol.

The distillate of the first reaction column (486.6 kg/h) contains 90.6 wt. % dimethyl carbonate, 8.2 wt. % methanol, 1 wt. % phenol and 0.2 wt. % anisole and is fed, together with a further stream (36.6 kg/h) containing 97.3 wt. % dimethyl carbonate and 2.7 wt. % methanol, to a refinery step consisting of two distillation columns for the purpose of separating the methanol from the dimethyl carbonate.

As the products of the methanol separation there are obtained 482 kg/h of a dimethyl carbonate fraction containing 98.75 wt. % dimethyl carbonate, 1 wt. % phenol, 0.2 wt. % anisole and 0.05 wt. % methanol, and 41 kg/h of a methanol fraction containing 99.5 wt. % methanol and 0.5 wt. % dimethyl carbonate.

Because methanol and dimethyl carbonate form an azeotropic mixture, separation of the mixture is carried out using the two-pressure process. In this process, the mixture is first heated to 137° C. in a preheater and is thereby also partially evaporated; then, in the first distillation column (K5)—which is also referred to as the dimethyl carbonate distillation column—it is first decomposed into the above-mentioned dimethyl carbonate fraction as bottom product and a fraction having an almost azeotropic composition (113.4 kg/h) containing 76.1 wt. % methanol and 23.9 wt. % dimethyl carbonate as distillate.

The dimethyl carbonate distillation column operates at a top pressure of 5.5 bar and a reflux ratio of 1.2 and has a rectifying section with 16 theoretical stages and a stripping section with 7 theoretical stages.

A temperature in the bottom of the column of 154.2° C. is thereby obtained. The required heat of evaporation is 59 kW. The evaporation of the bottom product takes place in two thermosiphon reboilers, the majority of the heat (46 kW) being exchanged in a thermosiphon reboiler which at the same time serves as the first condenser of the second reaction column. The remaining heat of evaporation is provided in a second recirculating evaporator by means of steam.

The heat exchanger for preheating the feed stream of the dimethyl carbonate distillation column at the same time serves as the second condenser of the second reaction column, the transferred amount of heat being 17 kW.

In a second distillation column (K6)—which is also referred to as the methanol distillation column—which operates at a top pressure of 700 mbar and a reflux ratio of 2.3, methanol is separated off as bottom product (41 kg/h; MeOH/DMC 99.5/0.5 wt. %). The distillate (72.3 kg/h), containing 62.4 wt. % methanol and 37.6 wt. % dimethyl carbonate, is fed to the dimethyl carbonate distillation column again.

The methanol distillation column has a separating capacity of 30 theoretical stages, which is divided equally between the rectifying section and the stripping section.

The heat required in the evaporator of the methanol distillation column (49 kW) is provided by the condensation of the vapors from the dimethyl carbonate distillation column. The condenser of the dimethyl carbonate distillation column accordingly at the same time serves as the evaporator of the methanol distillation column.

The example clearly shows how the energy consumption in the preparation of diphenyl carbonate can be markedly reduced by efficient heat integration.

Thus, in the first reaction column, by the use of an intermediate condenser, the heat requirement, including heating and evaporation of the starting materials, evaporation in the bottom of the column and heating of the reaction zone, is reduced from 183.3 to 131.3 kW, that is to say by 28.4%. At the same time, the consumption of cooling agent is reduced from 183.2 to 126.2 kW, accordingly by 31.1%.

By the heat integration of the second reaction column with the separation of the methanol/dimethyl carbonate mixture, the heating agent requirement for the separation of methanol and dimethyl carbonate is reduced from 76 kW to 13 kW, that is to say by 83%. At the same time, the cooling agent requirement of the second reaction column is reduced from 64 to 1 kW, that is to say by 98.4%.

Example 2

According to the Invention

Under otherwise identical conditions as in Example 1, the first reaction column is operated without an intermediate condenser.

By the heat integration of the second reaction column with the separation of the methanol/dimethyl carbonate mixture, the heating agent requirement for the separation of methanol and dimethyl carbonate can likewise be reduced from 76 kW to 13 kW, that is to say by 83%, however. At the same time, the cooling agent requirement of the second reaction column is reduced from 64 to 1 kW, that is to say by 98.4%.

Consequently, it is possible to make a considerable saving in terms of energy using the process according to the invention.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

What is claimed is:

1. A process comprising:
reacting a dialkyl carbonate of the formula (II) and an aromatic hydroxy compound of the formula (III) in the presence of a transesterification catalyst in a first reaction column, the first reaction column comprising a top section, a bottom section, a rectifying section in an upper portion of the column and a reaction zone below the rectifying section,

wherein $R^1$ and $R^2$ independently of one another represent linear or branched, optionally substituted $C_1$-$C_{34}$-alky,

wherein R, R' and R" independently of one another represent H, linear or branched, optionally substituted, $C_1$-$C_{34}$-alkyl, $C_1$-$C_{34}$-alkoxy, $C_5$-$C_{34}$-cycloalkyl, $C_7$-$C_{34}$-alkylaryl, $C_6$-$C_{34}$-aryl or a halogen radical, and wherein R can also represent —COO—R''', wherein R''' can be H, linear or branched $C_1$-$C_{34}$-alkyl, $C_1$-$C_{34}$-alkoxy, $C_5$-$C_{34}$-cycloalkyl, $C_7$-$C_{34}$-alkylaryl or $C_6$-$C_{34}$-aryl;

feeding a bottom product from the first reaction column to a further reaction column; the bottom product comprising a diaryl carbonate of the formula (I), an alkylaryl carbonate of the formula (IV), or both, and residual unreacted dialkyl carbonate and aromatic hydroxy compound; the further reaction column comprising a top section, a rectifying section in an upper portion of the column and a reaction zone below the rectifying section; and reacting the residual unreacted dialkyl carbonate and aromatic hydroxy compound in the further reaction column,

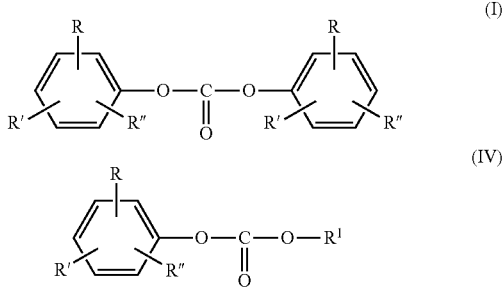

wherein R, R' and R" have the meaning given for formula (III), and wherein $R^1$ has the meaning given for formula (II);

feeding a process stream to a distillation column, the process stream comprising a mixture of unreacted dialkyl carbonate and one or more reaction-product alcohols drawn from the first reaction column, the further reaction column, or both, such that the unreacted dialkyl carbonate is separated from the one or more reaction-product alcohols; and recycling the separated, unreacted dialkyl carbonate to the first reaction column;

wherein the further reaction column comprises one or more condensers, and heat of condensation from the one or more condensers is fed back into the process.

2. The process according to claim 1, further comprising removing a vapor from the top section of the first reaction column, and wherein the process stream subjected to distillation comprises at least a portion of the vapor.

3. The process according to claim 1, further comprising removing a vapor from the top section of the first reaction column and condensing at least a portion of the vapor in a condenser to form a condensate, and wherein the process stream subjected to distillation comprises at least a portion of the condensate.

4. The process according to claim 1, wherein the rectifying section of the first reaction column comprises an intermediate condenser, and wherein heat of condensation from the intermediate condenser is fed back into the process.

5. The process according to claim 1, wherein the rectifying section of the first reaction column comprises a lower rectifying section, an upper rectifying section, and an intermediate condenser, wherein the intermediate condenser is disposed between the lower rectifying section and the upper rectifying section.

6. The process according to claim 1, wherein the rectifying section of the first reaction column comprises a lower rectifying section, an upper rectifying section, and an intermediate condenser, wherein the intermediate condenser is disposed between the lower rectifying section and the upper rectifying section, and wherein heat of condensation from the intermediate condenser is fed back into the process.

7. The process according to claim 1, wherein the one or more condensers of the further reaction column is disposed in the top section of the further reaction column.

8. The process according to claim 1, wherein at least a portion of the heat of condensation from the one or more condensers of the further reaction column provides heat for the separation of the unreacted dialkyl carbonate from the one or more reaction-product alcohols.

9. The process according to claim 4, wherein at least a portion of the heat of condensation from the one or more condensers of the further reaction column and the intermediate condenser of the first reaction column provides heat for the separation of the unreacted dialkyl carbonate from the one or more reaction-product alcohols.

10. The process according to claim 1, wherein at least a portion of the heat of condensation from the one or more condensers of the further reaction column provides heat for pre-heating of the dialkyl carbonate introduced into the first reaction column.

11. The process according to claim 4, wherein at least a portion of the heat of condensation from the one or more condensers of the further reaction column and the intermediate condenser of the first reaction column provides heat for pre-heating of the dialkyl carbonate introduced into the first reaction column.

12. The process according to claim 1, wherein at least a portion of the heat of condensation from the one or more condensers of the further reaction column provides heat for the separation of the unreacted dialkyl carbonate from the one or more reaction-product alcohols and heat for pre-heating of the dialkyl carbonate introduced into the first reaction column.

13. The process according to claim 4, wherein at least a portion of the heat of condensation from the one or more condensers of the further reaction column and the intermediate condenser of the first reaction column provides heat for the separation of the unreacted dialkyl carbonate from the one or more reaction-product alcohols and heat for pre-heating of the dialkyl carbonate introduced into the first reaction column.

14. The process according to claim 4, wherein at least a portion of the heat of condensation from the one or more condensers of the further reaction column provides heat for the separation of the unreacted dialkyl carbonate from the one or more reaction-product alcohols, and wherein at least a portion of the heat of condensation from the intermediate condenser of the first reaction column provides heat for pre-heating of the dialkyl carbonate introduced into the first reaction column.

15. The process according to claim 1, wherein the reaction zone of the first reaction column has a temperature of 100 to 300° C. and a pressure of 0.5 to 20 bar, and wherein the reaction zone of the further reaction column has a temperature of 100 to 300° C. and a pressure of 0.05 to 20 bar.

16. The process according to claim 1, wherein the reaction zone of the first reaction column has a temperature of 120 to 250° C. and a pressure of 0.8 to 15 bar, and wherein the reaction zone of the further reaction column has a temperature of 120 to 270° C. and a pressure of 0.1 to 10 bar.

17. The process according to claim 1, wherein the reaction zone of the first reaction column has a temperature of 150 to 240° C. and a pressure of 0.9 to 10 bar, and wherein the reaction zone of the further reaction column has a temperature of 180 to 250° C. and a pressure of 0.2 to 5 bar.

18. The process according to claim 1, wherein the dialkyl carbonate comprises dimethyl carbonate, diethyl carbonate or a mixture thereof, wherein the aromatic hydroxy compound comprises phenol, and wherein the diaryl carbonate comprises diphenyl carbonate.

* * * * *